(12) United States Patent
Kurzrock et al.

(10) Patent No.: US 11,434,534 B2
(45) Date of Patent: Sep. 6, 2022

(54) OPTIMIZING THERAPEUTIC OPTIONS IN PERSONALIZED MEDICINE

(71) Applicant: CureMatch, Inc., San Diego, CA (US)

(72) Inventors: Razelle Kurzrock, San Diego, CA (US); Igor Flint Tsigelny, San Diego, CA (US); Amélie Clémence Boichard, San Diego, CA (US); Sergey Kozhenkov, La Jolla, CA (US); Kevin Toivo Bush, San Diego, CA (US); Timothy Viet Pham, Anaheim, CA (US); Stephane Richard, San Diego, CA (US)

(73) Assignee: CureMatch, Inc., San Diego, CA (US)

( * ) Notice: Subject to any disclaimer, the term of this patent is extended or adjusted under 35 U.S.C. 154(b) by 134 days.

(21) Appl. No.: 16/331,953

(22) PCT Filed: Sep. 8, 2017

(86) PCT No.: PCT/US2017/050805
§ 371 (c)(1),
(2) Date: Mar. 8, 2019

(87) PCT Pub. No.: WO2018/049250
PCT Pub. Date: Mar. 15, 2018

(65) Prior Publication Data
US 2019/0233895 A1    Aug. 1, 2019

Related U.S. Application Data

(60) Provisional application No. 62/385,192, filed on Sep. 8, 2016.

(51) Int. Cl.
G06F 15/173 (2006.01)
C12Q 1/6883 (2018.01)
G16H 10/60 (2018.01)
(Continued)

(52) U.S. Cl.
CPC ............. *C12Q 1/6883* (2013.01); *C12Q 1/68* (2013.01); *G06F 15/173* (2013.01);
(Continued)

(58) Field of Classification Search
CPC ........ G16H 10/60; G16H 20/10; G16H 50/20; C12Q 2600/156; C12Q 1/6883; G06F 15/173
(Continued)

(56) References Cited

U.S. PATENT DOCUMENTS

2001/0034023 A1 * 10/2001 Stanton ............... C12Q 1/6883
435/6.16
2005/0256745 A1 * 11/2005 Dalton .................. G06Q 40/08
705/3

(Continued)

FOREIGN PATENT DOCUMENTS

WO    2007/064675 A1    6/2007
WO    2010/028288 A2    3/2010
(Continued)

OTHER PUBLICATIONS

Pannu, Avneet. "Artificial intelligence and its application in different areas." Artificial Intelligence 4.10 (2015): 79-84.*

*Primary Examiner* — Mark Holcomb
(74) *Attorney, Agent, or Firm* — Torrey Pines Law Group, PC

(57) ABSTRACT

In an aspect, a method includes obtaining patient data for a patient, the patient data including one or more molecular biomarkers specific to the patient, standardizing and curating the patient data, classifying the standardized and curated patient data including classifying the one or more molecular biomarkers by one or more of its functional effects, using the one or more functional effects for the one or more molecular biomarkers to identify a combination of available therapeu-
(Continued)

tic options by targeting biomarkers with relevant functional effects based on the patient data, applying a learning method to optimize results for presentation to a user, and presenting optimized results to the user.

11 Claims, 24 Drawing Sheets

(51) Int. Cl.
| | |
|---|---|
| *G16H 20/10* | (2018.01) |
| *C12Q 1/68* | (2018.01) |
| *G06Q 10/10* | (2012.01) |
| *G16H 50/50* | (2018.01) |
| *G16H 20/60* | (2018.01) |
| *G16H 50/20* | (2018.01) |

(52) U.S. Cl.
CPC ........... *G06Q 10/101* (2013.01); *G16H 10/60* (2018.01); *G16H 20/10* (2018.01); *G16H 20/60* (2018.01); *G16H 50/50* (2018.01); *C12Q 2600/156* (2013.01); *G16H 50/20* (2018.01)

(58) Field of Classification Search
USPC .......................................................... 705/2–4
See application file for complete search history.

(56) References Cited

U.S. PATENT DOCUMENTS

| | | | | |
|---|---|---|---|---|
| 2006/0160071 | A1* | 7/2006 | Heckerman | G16B 30/10 435/5 |
| 2011/0301859 | A1 | 12/2011 | Carter | |
| 2013/0268290 | A1* | 10/2013 | Jackson | G16H 70/60 705/2 |
| 2015/0347699 | A1* | 12/2015 | Vidwans | G16H 50/20 705/2 |

FOREIGN PATENT DOCUMENTS

| | | |
|---|---|---|
| WO | 2012/122347 A1 | 9/2012 |
| WO | 2014/089241 A2 | 6/2014 |
| WO | 2014/117873 A1 | 8/2014 |

* cited by examiner

Patient Info:
Patient ID: Mr./Mrs. J. Doe
Diagnosis: Name of the disease & pathology description Actionable Alterations

| Gene | Alteration | Effect |
|---|---|---|
| Marker 1 | Alteration 1 | Has an effect on the disease's outcome |
| Marker 2 | Alteration 2 | Has an effect on the disease's outcome |
| Marker 3 | Alteration 3 | Has an effect on the disease's outcome |
| Marker 4 | Alteration 4 | Has an effect on the disease's outcome |

Non-Actionable Alterations

| Gene | Alteration | Effect |
|---|---|---|
| Marker 5 | Alteration 5 | Does not have an effect on the disease's outcome |

Best Combinations of (N) Drugs or Less

| Score | Drugs combination | Target(s) | On-Label? | Contraindications |
|---|---|---|---|---|
| +++++ | Drug 1 + Drug 2 | Target 1 + Target 2 | Indicated in the disease | |
| +++ | Drug 2 + Drug 3 | Target 2 + Target 3 | Indicated in the disease | |
| + | Drug 2 | Target 2 | Indicated in the disease | |
| +/- | Drug 3 + Drug 4 | Target 3 + Target 4 | Indicated in another disease | |
| +/- | Drug 3 + Drug 4 + Drug 5 | Target 3 + Target 4 | Not indicated | Contraindicated in case of xxx. |

FIG. 9B

OPTIMIZING THERAPEUTIC OPTIONS IN PERSONALIZED MEDICINE

CROSS-REFERENCE TO RELATED APPLICATIONS

This application claims priority from U.S. Provisional Application Ser. No. 62/385,192 filed on Sep. 8, 2016, which is incorporated herein by reference in its entirety.

FIELD

The present disclosure generally relates to devices, systems, and methods for improving personalized medicine, and more specifically to stratifying, combining, and optimizing therapeutic options in personalized medicine.

BACKGROUND

Personalized medicine involves the use of molecular markers to guide treatment regimens adapted to each patient, e.g., in order to overcome problems of toxicity and therapeutic resistance encountered with empirical medicine. Multiple examples of correlations between single treatment efficacy and the presence or absence of molecular markers in a patient sample have been described, but monotherapy may still present a lack of efficiency in multifactorial diseases, such as multi-genic diseases. There remains a need for techniques to give health care providers an optimal choice of combinatorial therapies, considering criteria such as molecular markers accuracy, drugs efficiency, drugs approvals, drug-drug interactions, drug-condition interactions, contraindications and other medical, as well as socioeconomics considerations.

SUMMARY

In an aspect, a method includes obtaining patient data for a patient, the patient data including one or more molecular biomarkers specific to the patient, standardizing and curating the patient data, classifying the standardized and curated patient data including classifying the one or more molecular biomarkers by one or more of its functional effects, using the one or more functional effects for the one or more molecular biomarkers to identify a combination of available therapeutic options by targeting biomarkers with relevant functional effects based on the patient data, applying a learning method to optimize results for presentation to a user, and presenting optimized results to the user. The learning method may include at least one of a first learning method and a second learning method. The first learning method may include querying a clinical outcome database for similar cases, the clinical outcome database including records comprising a diagnosis, a set of biomarkers, one or more prescribed drugs, and an outcome obtained after treatment by the one or more prescribed drugs, comparing the identified combination of available therapeutic options to the similar cases, and eliminating combinations that do not satisfy a threshold of similarity. The second learning method may include comparing the identified combination of available therapeutic options to an efficiency of one or more similar drug combinations based on an experimental model.

In another aspect, a method for generating a personalized combinatorial therapy regimen includes obtaining one or more samples from a subject, preparing the one or more samples, determining a status of one or more molecular markers in the one or more samples, and stratifying one or more therapeutic options based on the status of the one or more molecular markers, where stratifying includes an evaluation of a molecular marker status relevance and a selection of approved or recommended drugs predicted to be efficacious and safe in regard to the status of the one or more molecular markers. The selection may be based on results given by a decision-making machine where the decision-making machine is querying a database including one or more of: in silico functional analysis of alterations, publicly reported functional impacts of alterations, publicly reported markers-pathways interactions, publicly reported drugs-markers interactions (marker actionability), publicly reported drugs approvals and recommendations, publicly reported drugs toxicity, publicly reported drugs contraindications, publicly reported pharmacogenomics markers of drug response, and user-specific set of available drugs. The decision-making machine may use a set of drug-stratification rules updated on a predetermined basis by a supervised-learning machine. The method may also include combining one or more therapeutic options where the combining includes a generation of possible combinations of available drugs predicted to be efficacious and safe in regard to the status of the one or more molecular markers. The method may further include stratifying one or more combinations of drugs where the stratifying includes a generation of a combination's score and a sorting of combinations by score, by query of a database including one or more of: drug-drug interactions and incompatibilities, drug-drug activities redundancies, drug-drug pharmacology class redundancies, dosage adaptation data. The stratifying may also include application of an algorithm encompassing a set of specific processing steps regularly updated on a predetermined basis by the supervised-learning machine. The method may also include reducing a number of combinations generated by the decision-making machine where the reducing includes filtering of a combinations' data flow to preserve computing performances. The method may further include providing an interactive user web-interface where interactivity of the user web-interface includes one or more of: entering data, modifying one or more combinatory processing steps, evaluating combinations proposed, and retrieving previous results. The method may also include providing a printable report based on user's preferences and selections, collecting retrospective and prospective results records, and inferring retrospective and prospective results records in a supervised-learning process where inferring includes adapting decision-making machine by tuning databases, drug-stratification rules, and combinatory processing steps.

These and other features, aspects and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

FIG. 9B illustrates an example of a report.

DETAILED DESCRIPTION

Figure 1A:
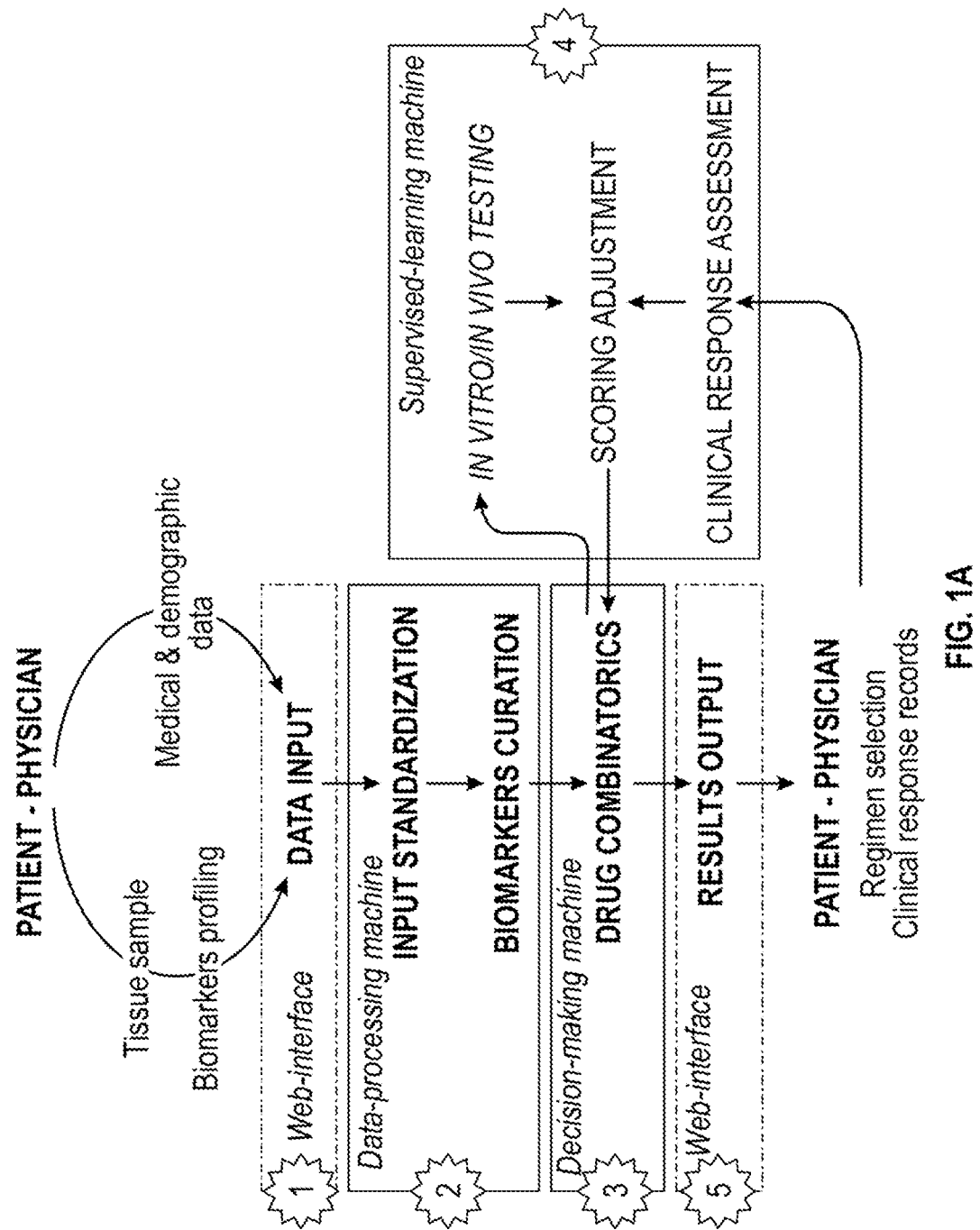
FIG. 1A illustrates a system architecture for personalized medicine.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless specifically stated to the contrary.

In general, the devices, systems, and methods relate to improvements in personalized medicine. Personalized medicine, also called "molecular-based medicine," generally involves the use of molecular biomarkers to guide treatment regimens adapted to each patient, e.g., thereby overcoming and/or reducing the problems of toxicity and therapeutic resistance encountered with treatment regimens developed through empirical, evidence-based medicine.

The molecular markers used to guide personalized medicine may be of several different types. They can be derived from genomic (e.g., DNA alterations), epigenomic (e.g., DNA methylation alterations), transcriptomic (e.g., RNA alterations including but not limited to coding RNAs and non-coding RNAs), proteomic (e.g., protein alterations), metabolomic (e.g., metabolite level alterations), or biochemistry (e.g., chemicals level alterations). These molecular markers can be detected in normal/healthy tissues, pathologic tissues (such as benign or malignant tumors), or pathogen-related entities (e.g., bacteria, virus, and the like). They can also be inherited (germline molecular patterns) or arise de novo in an individual (e.g., after-birth, somatic molecular patterns) which could occur after a particular environmental exposure (e.g., tobacco smoke, pollutants, and so on).

Personalized medicine can generally be applied to any and all medical fields, including but not limited to oncology, immunology, neurology, infectious disease, and psychiatry. A patient benefitting from personalized medicine may suffer from a proliferative disease (e.g., cancer, psoriasis, benign tumors, and the like), a degenerative disease (e.g., Alzheimer's disease, Parkinson's disease, and the like), a metabolic disease (e.g., diabetes, heart diseases, neurological disorders, and the like), or an infectious disease (e.g., AIDS, viral hepatitis, bacterial meningitis, and the like).

The benefits of personalized medicine in patient care may be observed over a short-term (e.g., emergency cases) or a long-term period (e.g., indolent diseases), and may be based on survival (in the case of life-threatening diseases), healthiness/recovery (in the case of non-life-threatening diseases), well-being (in the case of palliative care), or behavioral (in the case of problem behavior—e.g., self-harming behavior, emotive behavior, and the like) criteria.

Therapeutic options used in personalized medicine may be the same as those used in empirical medicine and include chemicals, enzymes, antibodies, proteins, non-chemical (e.g., radiation), and substances commonly used but not referenced as drugs (e.g., coffee, food, probiotics, and the like).

An overview of a system for personalized medicine will now be described. The system may be used for stratifying, combining, and optimizing therapeutic options in personalized medicine.

Although a wealth of scientific literature exists describing the correlation between single treatment efficacy and the presence or absence of molecular markers in a patient sample, the selection of the appropriate drug remains largely based on empirical data. Techniques presented herein may provide health care personnel with a computationally-based approach for determining the optimal choice of combinatorial therapies targeting a particular patient's disease, his/her genomic, proteomic, transcriptomic, and metabolomic profile. Techniques may not only take into account patient-specific criteria such as medical and family history, but also may consider molecular markers accuracy, drug efficiency, drug regulatory approvals, drug-drug interactions, drug-condition interactions, contraindications, as well as other medical and socioeconomic considerations.

In brief, a decision support system presented herein may be used to apply concepts of personalized medicine in patient care, regardless of the molecular marker types, the origin of the sample, the medical area, and the disease history.

FIG. 1A illustrates a system architecture for personalized medicine. The system may in general include at least five distinct modules—a data input module (Module 1), a data processing module (Module 2), a decision making module (Module 3), a supervised learning module (Module 4), and a results output module (Module 5).

In general, the figure shows an overall workflow of machines and modules that may be used by a system for personalized medicine. As shown in the figure, a user (physician) may request a service by entering clinical and molecular data relevant to a patient using a user-interface (Module 1—input). Entered data may be standardized and curated in order to keep only relevant information and to define the set of drugs targeting the biomarkers of interest for the data-processing machine (Module 2). The decision-making machine (Module 3) may use a complex set of specific processing instructions (combinatorial rules) on the set of usable drugs from the data processing machine to synthesize drug combinations and stratify these proposed therapy regimens specific to the patient's data. The results of the decision-making machine may be constantly adjusted by a supervised-learning machine (Module 4), using a constantly updated database of clinical response and in vitro/in vivo testing observations. The user can retrieve the generated results (therapeutic recommendations) using the same user-interface as used for input (Module 5—output).

More specifically, the system may include a web interface allowing a user (e.g., physician) to order a new service, to enter clinical and molecular data relating to this service (data input—Module 1) and to retrieve previously generated results (results output—Module 5). The entered information may be transmitted to a data-processing machine (Module 2), which uses synonym and keyword databases to standardize the names of, e.g., genes/proteins, genetic alterations, drugs, and diagnoses. Additional steps facilitating medical coding, medical billing, or configuration of the system to a level of service chosen by the user can also be performed. The standardized molecular profile may be further filtered using data present in the knowledgebase for exclusive biomarkers relevant to a therapeutic decision ("biomarkers of interest" or "actionable biomarkers"). Next, the data may be input into a decision-making machine (Module 3), which uses a method of prediction based on available scientific results and therapeutic recommendations, as well as biological, pharmacological, and medical expert knowledge to define the set of drugs targeting these biomarkers. A complex system of specific processing instructions may be used to combine and stratify therapeutic regimens specific to the patient's data, resulting in a list of drug combinations targeting one or more biomarkers of interest. These combinations may be sorted by biochemical and clinical efficiency, as well as by relevant criteria such as patient's access to certain medications or the patient's medical history. The potentially large number of combinations may be reduced by a statistical data-reduction module. The results given by the decision support system may be constantly adjusted by a supervised-learning machine (Module 4) using a regularly updated database, providing an optimization method based on clinical response (information obtained from patients already treated) and case-by-case in vitro and/or in vivo testing experiments on edited cell lines and/or animal models.

Figure 1B:
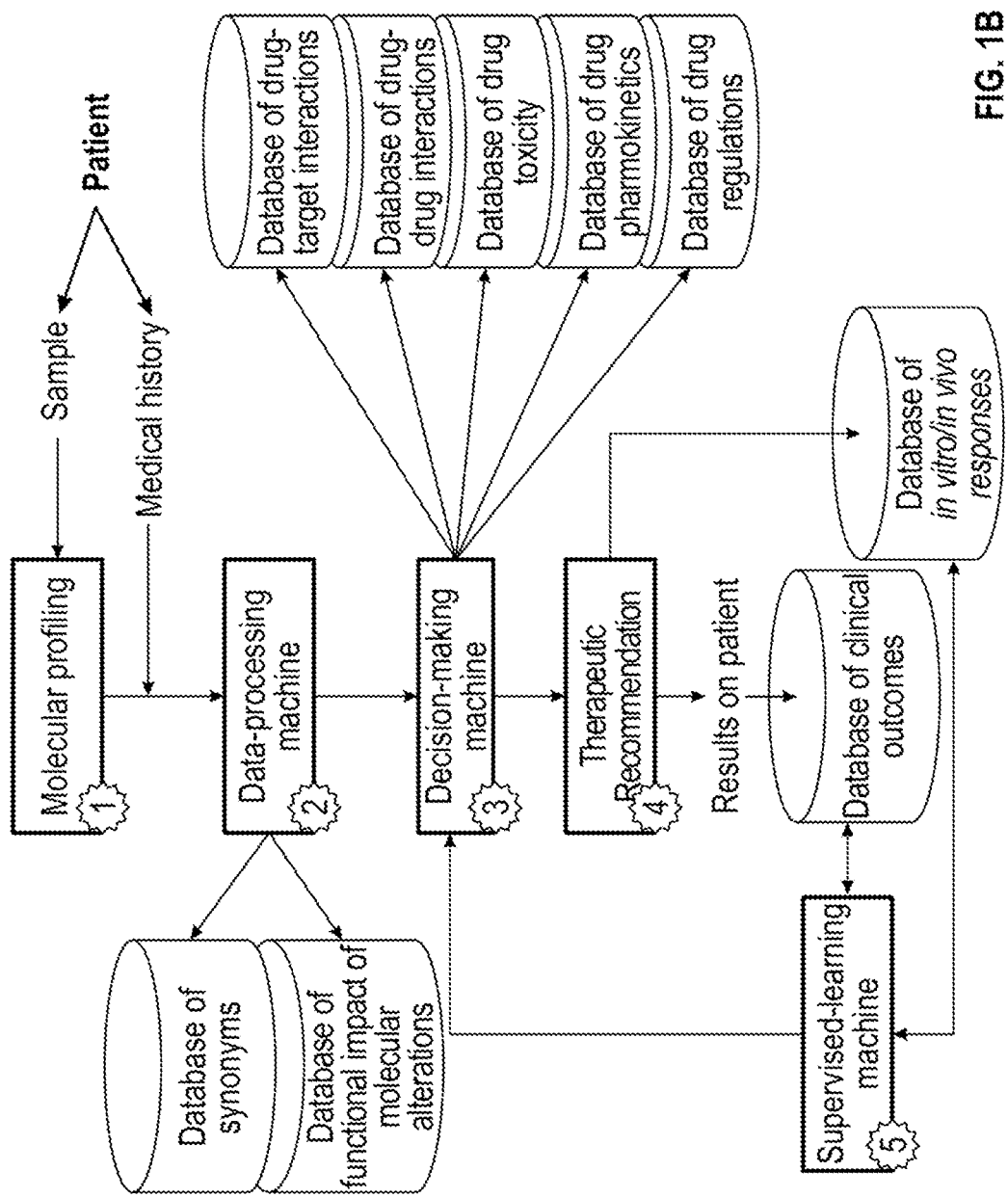
FIG. 1B illustrates a method for personalized medicine.

FIG. 1B illustrates a method for personalized medicine. This figure provides an overview of a method that may be used in a system such as that shown in FIG. 1A.

As shown in the figure, molecular profiling results and supplemental clinical information may be provided to the data-processing machine. Within the data-processing machine, databases of keywords and synonyms may be used to standardize the input and databases of functional impact may be used to determine and retain relevant alterations. These alterations may be submitted to the decision-making machine, which queries databases of drug targeting, drug interactions, drug toxicity, and drug regulations to formulate appropriate drug combinations, respecting a set of specific processing instructions. The decision-making machine may provide therapeutic recommendations for the physician to treat his/her patient. Optionally, the physician can provide feedback of the clinical results of using the drug combination regimen they chose for their patient. This information may be used by the supervised-learning machine to improve the system. Additionally, the efficiency of the combination chosen may be tested in vitro on edited cell lines or in vivo on animal models. The results of these experiments could also be used by the supervised-learning machine.

Figure 1C:
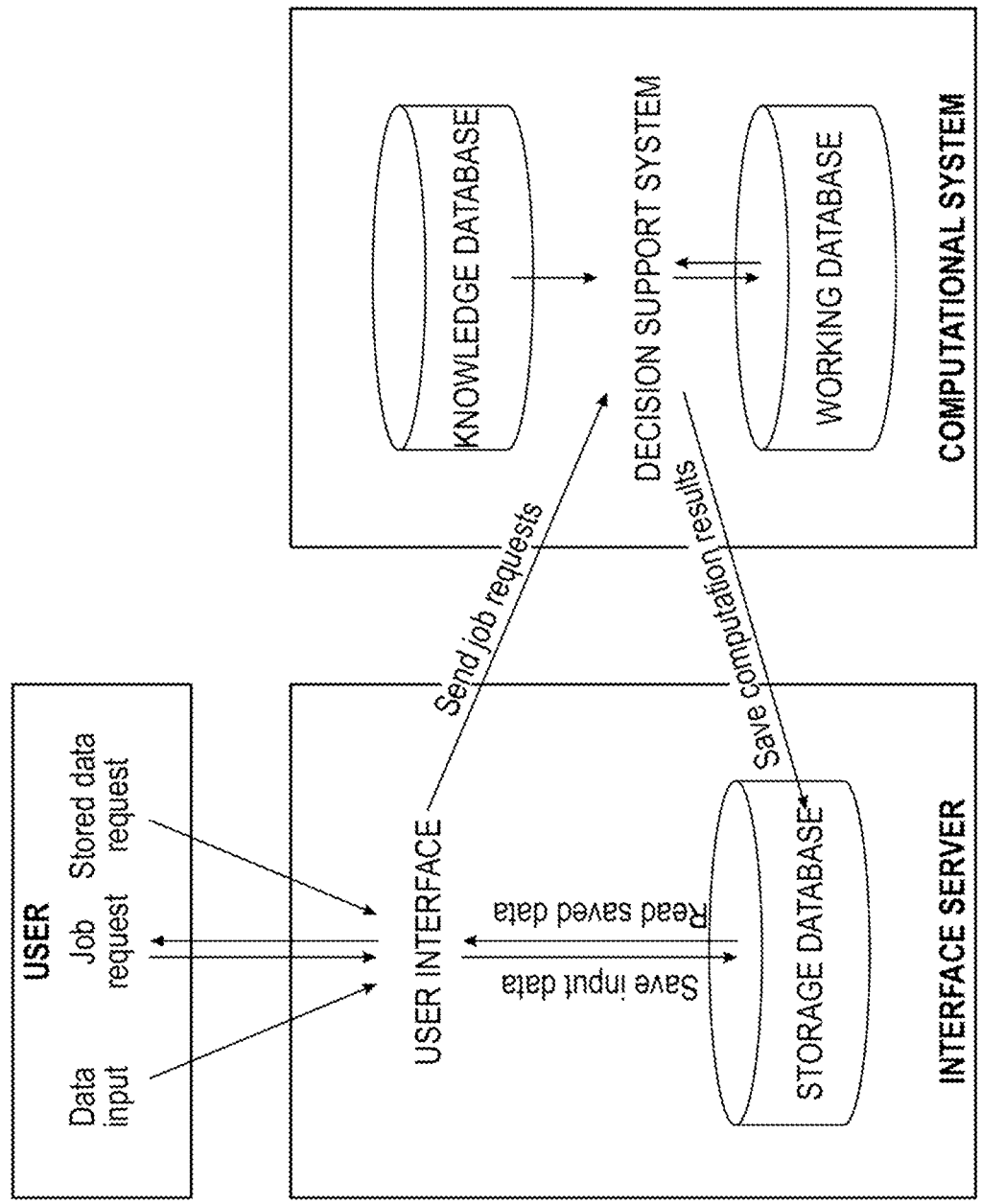
FIG. 1C illustrates a system computational architecture for personalized medicine.

FIG. 1C illustrates a system computational architecture for personalized medicine. Specifically, the figure shows a functional block diagram of a system architecture (such as that shown in FIG. 1A) including the physical location of various components. The figure may represent the system of FIG. 1A at the informatics level. The system may include an interface side and a computational side. In an aspect, there are at least two machines, with at least one in each category (more machines may help increase system availability and ability to handle high job loads). The interface side may include a software-based user interface connected to a storage database. A user may interact with the system by inputting patient data into the user interface, requesting jobs (e.g., making requests for computational jobs), and searching for stored data (e.g., searching and/or viewing data from the stored database in a human-readable format). Job requests may contain user-defined parameters and inputted data. Job requests may be sent from the interface to the decision support system on the computational side. The computational side may include a decision support system, a knowledge database, and a working database meant to store the flow of data generated during the computation processes. In other words, the computational side may utilize a knowledge database including curated biological data, as well as a working database meant to store data generated during the computational processes. The decision support system may read data from the knowledge database, and read and write data generated as a byproduct of the combinatorial computations into the working database. The decision support system final output (e.g., comprising a list of drugs combinations) may be sent back to the interface server and stored into the storage database. This data (e.g., combination output data) can be retrieved upon request by the user through interacting with the interface.

The first module (Module 1) may include data input as discussed above, e.g., through a web interface or the like. Thus, the decision support system discussed herein may be accessed via a secure web interface. All processes leading to the generation of the final results may be ordered locally or at distance, using the user's interface.

Figure 2:
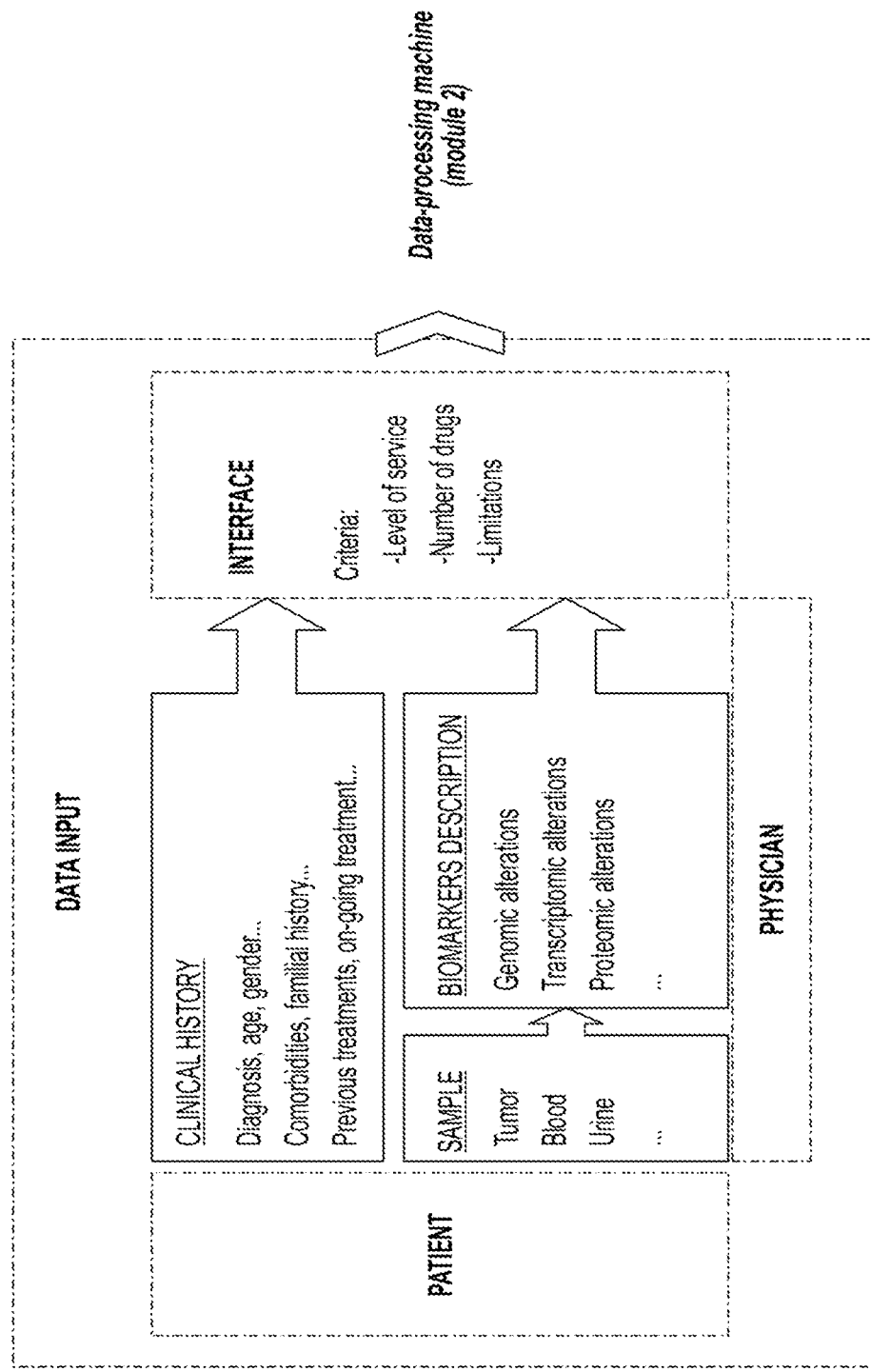
FIG. 2 illustrates a user's data input.

FIG. 2 illustrates a user's data input. The figure shows the origin and the type of patient data that may be entered into Module 1 of a system. By way of example, a patient may visit a healthcare provider that records medical history and collects a sample suitable for molecular analysis. Molecules of interest (e.g., DNA, RNA, proteins, or the like) may be extracted from the sample and sent to a specialized laboratory to perform molecular profiling. Molecular results, clinical data, and user-defined parameters may be inputted in the system using a user-based interface.

Thus, in a first step, data may first be obtained. Using the example above, a patient may visit a physician, who obtains and records informative medical and demographics data (e.g. age, gender, histological diagnosis, previous treatment(s), current treatment, medical history and comorbidities, familial history and inherited syndromes, and the like) and performs a biopsy (tumor, blood, tissue of interest, body fluid, or the like) in order to define the status of molecular biomarkers specific to the patient's disease. The status of molecular biomarkers can be obtained from a validated third party company or an in-house laboratory, and can be assessed using methods of genomic profiling (e.g., DNA sequencing, comparative genomic hybridization, in situ hybridization, and the like), epigenomics profiling (e.g., histone modification assay, chromatin immunoprecipitation, restriction landmark analysis, bisulfite sequencing, and the like), transcriptomic profiling (e.g., microarray, RNA sequencing, real-time polymerase amplification, and the like), proteomic profiling (e.g., immunoassay, mass spectrometry, and the like), metabolomics profiling, or biochemistry profiling.

Next, data may be inputted. The physician (or designate) may log in to the system's web interface and enter information relevant to the system's use such as patient identification, patient diagnosis, patient treatment, and molecular description. At this stage, the physician may order a level of service depending of the type of results needed (e.g., de novo combination calculation or confirmation of a regimen already in use, consultation of previous results, level of confidence used to generate the results, etc.) and choose the maximum number of drugs to use.

The second module (Module 2) may include data processing, e.g., using a data-processing machine. In an aspect, after completion of a manual input of data, the system prepares the data for the decision-machine process. This step may include standardizing and curating the input data (e.g., medical, demographics, and molecular descriptions).

Figure 3:
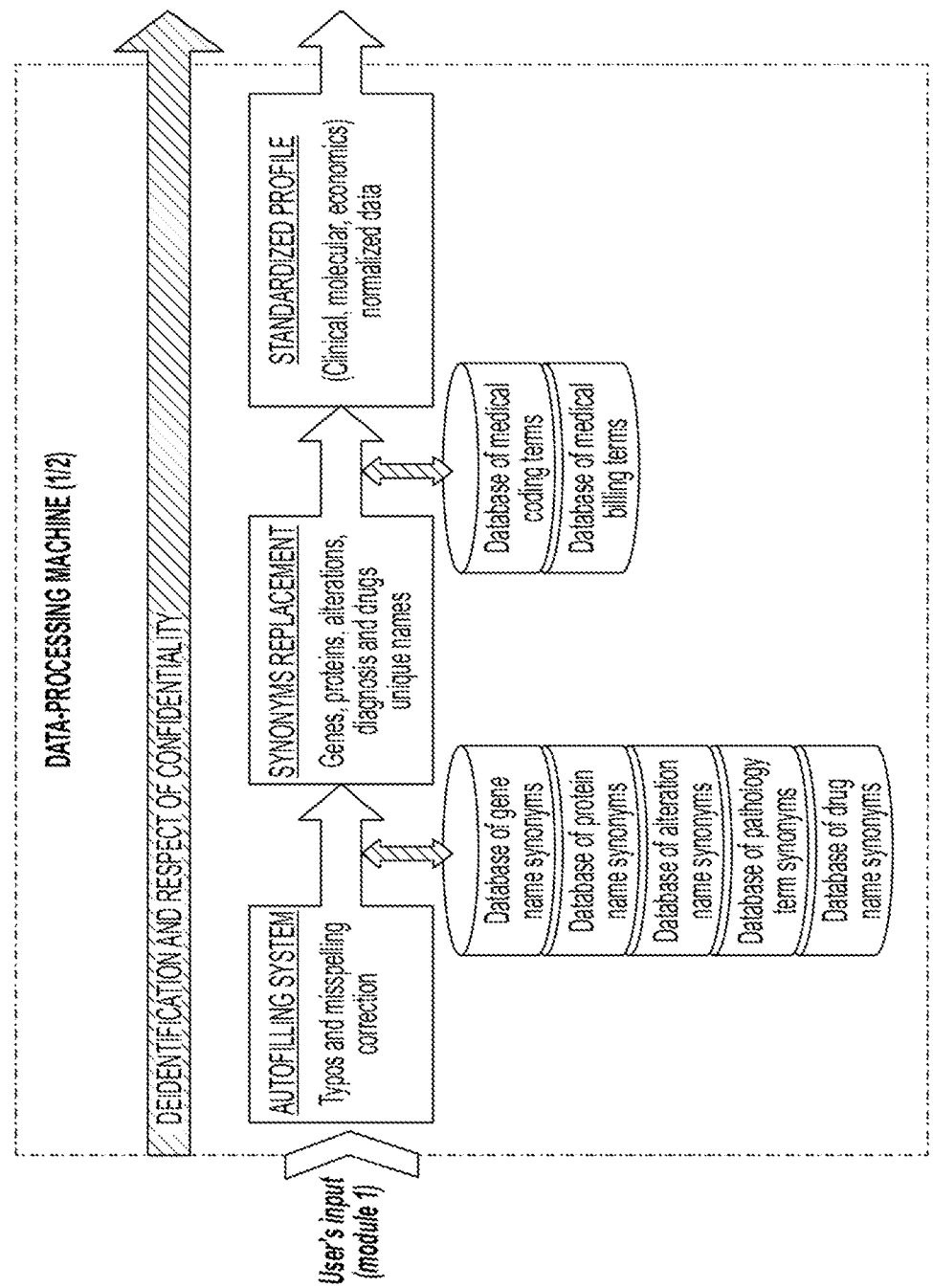
FIG. 3 illustrates automated data input standardization.

FIG. 3 illustrates automated data input standardization. The figure shows a method that may be used during the first step of the data-processing machine.

Data entered by the user may be checked for typographical errors or misspelling errors. All biologically relevant names (e.g., genes, proteins, alterations, pathology, and drugs) may be normalized using databases of synonyms where the system replaces input names with a unique reference name. A user can also perform additional steps relating to medical coding, medical billing, or configuration of the decision-making machine to a specific chosen level of service. Security features may be implemented in order to respect the confidentiality of protected health data and to ensure its safe usage of the protected health data throughout all steps in the process.

In general, the figure shows that several methods may be used to standardize the input while preserving data integrity by avoiding any lost, inaccurate, and redundant information.

The web interface may incorporate an automatic filling system, e.g., that points out any typographical errors or misspellings as stated above. Then, the analysis unit may query databases of synonyms to obtain unique names of genes, alterations, proteins, diagnosis, and drugs corresponding to the patient's description (e.g., when several terms exist for the same object). The system may replace all commonly used synonyms by a same, unique, reference name. For all of the following steps, the system may use the official gene names provided by the HUGO Gene Nomenclature Committee (HGNC), as well as world-wide used drug generic names.

The standardization of a user's input may also take into account socioeconomic factors, such as medical codes (using ICD coding system) and medical billing information (depending on the level of services chosen and the health insurance details provided). Every component of the input standardization procedure and all subsequent procedures may respect the mandatory medical confidentiality requirements (e.g., Health Insurance Portability and Accountability Act (HIPAA) law in United States) and the entire system may have specific security features ensuring the safe use of protected health information (PHI).

Figure 4:
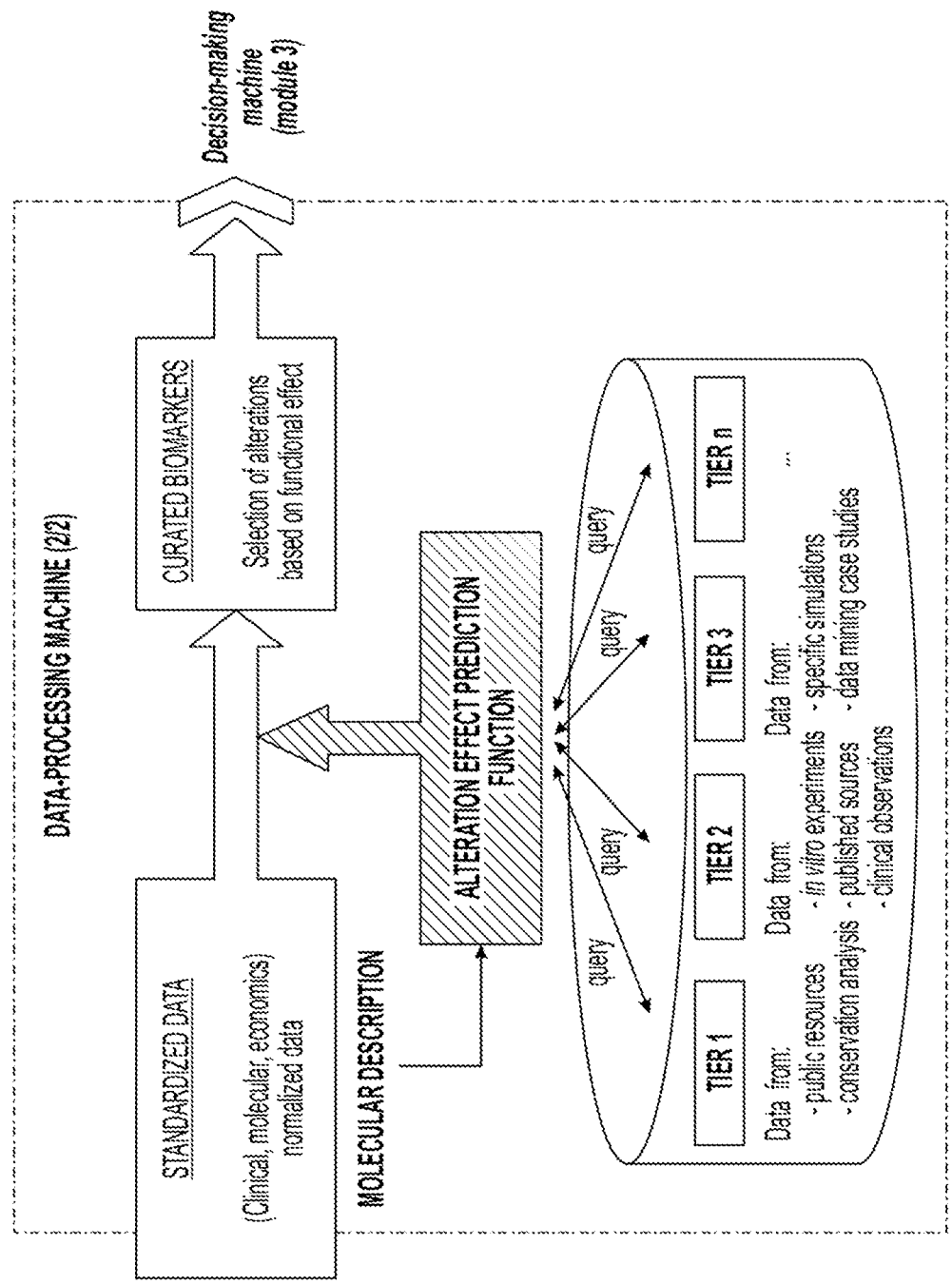
FIG. 4 illustrates impact assessment and curation.

FIG. 4 illustrates impact assessment and curation. Specifically, the figure shows an example of the alteration's functional impact assessment and curation in Module 2 of a system such as that shown in FIG. 1A. In other words, the figure shows method elements that may be used in the second step of the data-processing machine. In general, this may include the molecular description being transferred to a unit classifying the biomarkers' alterations by their functional effects. This module may interact with a database of gene functional effect information. This database may have a tiered structure. All data, regardless of tier, may be in the form of serialized data structures. Tiers may represent levels of significance and/or levels of service and the number of tiers can be changed according to the system's usage. Different functional effects may exist for a same alteration, reflecting the number of different data sources. A set of specific processing instructions may define a final unique conclusion to attribute to each alteration, taking into account the number of tier(s) to consider and the possible discrepancies existing between tiers. Only alterations considered functionally impacting the disease course may be transmitted to the decision-making machine.

The result of the input standardization may thus be transferred to a unit classifying the biomarkers' alterations by their functional effects as shown in the figure. This module may interact with a database of gene functional effect information, where the database may have a tiered structure, and where the data is in the form of serialized data structures. Each serialized structure may include the gene name or protein name, the specific description of the aberration (including, but not limited to, DNA level, RNA level, and protein level alterations), identifiers (including, but not limited to, genomic accession numbers and database identifiers) and a conclusion regarding the alteration's effect. The number of tiers can be modulated accordingly to the system's usage and may reflect different levels of significance and/or different levels of service. For example, in a model using three tiers, the first (lowest) tier may contain data with effect conclusions determined by basic analysis of protein regions and conserved sequences, e.g., extracted from public resources. The second tier may include data with effect conclusions determined through in vitro/in vivo experimentations, clinical observations, and published observations. The third tier may include data with effect conclusions determined by case studies and in-depth computer structure-activity modeling and simulations.

Different conclusions may exist for a same alteration, reflecting the number of data sources. A set of specific processing instructions may define a final unique conclusion for each alteration, taking into account all serialized conclusions and levels of significance known for said alteration. The nature of the final conclusions may depend on the disease studied and may dictate the relevance of the biomarker for the specific case. For example, in a case of cancer, the alteration effect may be summarized as 'oncogenic,' 'non-oncogenic,' 'unknown,' or 'conflicting.' Only alterations presenting an 'oncogenic' or 'unknown' functional effect may be kept for further consideration by the system (in this example).

FIG. 4 may thus represent a 'biomarkers curation' of sorts.

As stated above, Module 3 in a system such as that shown in FIG. 1A may include a decision-making machine or the like.

Using the functional effects for each biomarker, the decision-making machine may apply specific processing instructions in order to define, and provide the user, the best combinations of available therapeutic options targeting as many biomarkers with a relevant effect on the disease progression as possible, preferably all.

Figure 5A:
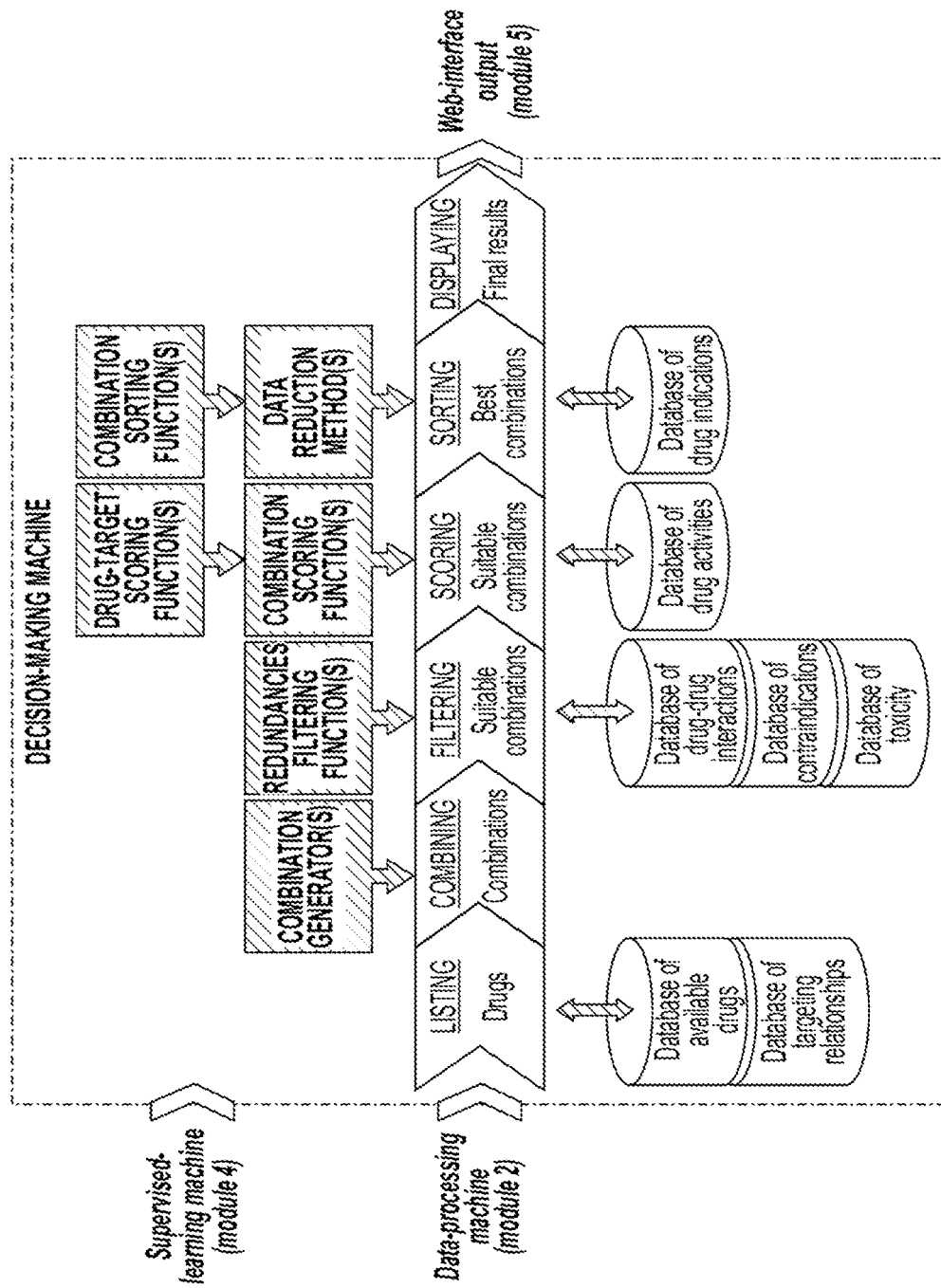
FIG. 5A illustrates processing instructions used by a decision-making machine.

Therapeutic options may include agents targeting the biomarker itself ("direct" targeting) or a component within the biomarker's canonical signaling pathway(s) ("semi-direct" or "indirect" targeting). For example, a drug "directly" inhibiting a ligand of a biomarker may be considered "semi-directly" targeting the biomarker, and a drug 'directly' targeting a molecule downstream of the biomarker's signaling pathway may be considered 'indirectly' targeting the biomarker FIG. 5A illustrates processing instructions used by a decision-making machine. The figure shows a functional diagram of an example of data flow over several steps in a decision making machine.

First, standardized input data may be used to determine all possible drugs for the given targets using information available in the accessible drugs and targeting relationships databases. These possible drugs may then be used with input parameters to generate every possible combination for the patient. The list of combinations may then be filtered for unacceptable conditions such as contraindications, redundant targeting, and toxicity, using specific functions and a set of appropriate databases. Retained (suitable) combinations may be scored, where the score of each combination is primarily based on the drugs' biological activity. The scored combinations may then be sorted by numerical scores and other desirable features such as indications and availability. The ordered list of combination may then be returned to the user-interface for display to a user.

Processing instructions and drug combinatorics will now be discussed.

The decision-making machine may use a sequence of at least six processing steps as shown in the figure (e.g., listing, combining, filtering, scoring, sorting, and displaying). The sequence of the filtering, scoring, and sorting processing steps may be rearranged in order to improve the calculation's efficiency. All of these steps may be adjusted by the supervised-learning machine described herein.

The first processing step may include listing available and suitable drugs which may be used in the following combinatorics step. The list of relevant molecular biomarkers generated by the data-processing machine may be used to query a database of targeting relationships ('direct,' 'semi-direct,' or 'indirect') and attribute a specific way to target each alteration. The targeting relationships may be used to find corresponding drugs, e.g., using a database of available drugs, which may include local, United States, or foreign regulatory authorities' approved-drugs (e.g., Food and Drug Administration in United States, European Agency for Medicines in Europe, and so on), experimental drugs, or the user's self-designed compounds library.

The second processing step may include combining available and suitable drugs in order to produce therapeutic regimens acting on one or several molecular alterations presented by the patient. These combinations may be generated by different methods. For example, combinations may be built by selecting at least one drug for each existing target, leading to a complete coverage of all molecular alterations (but potentially increasing the toxicity through the high number of drugs used) (see FIG. 5B), or by defining a maximum number of drugs to combine, leading to a lower level of toxicity but potentially presenting a lack of efficiency due to an incomplete coverage of molecular alterations (see FIG. 5C).

The third processing step may include filtering potentially unwanted combinations of drugs, such as combinations presenting a high level of toxicity based on knowledgebase data or predictable negative interactions. Predictable negative interactions may be retrieved by querying specific databases (e.g., databases of contraindications, database of drug-drug interactions, database of side effects, and the like), whereas other filters may be implemented via an instruction process, such as the management of targeting redundancies. A targeting redundancy may be defined as multiple drugs used in the same combination that act on the same subset of targets in any form, directly, semi-directly, or indirectly (see FIG. 5D). In an aspect, targeting redundancies should be avoided since they increase the risk of toxicity and the treatment cost (through the use of excessive and/or unnecessary drugs). All combinations presenting an unacceptable redundancy may be excluded from the final results by the redundancy filtering process (see FIG. 5E) and only suitable combinations are kept.

The fourth processing step may include scoring the combinations of drugs. The efficiency/toxicity balance of each combination may be quantified by a scoring method, taking into account criteria such as the biochemical activities of each of the drugs used in that particular combination upon their respective targets, as well as advantage and penalization factors. For example, an advantage factor may be applied when the combination uses easy-to-access drugs or drugs indicated in the disease of concern, and a score may be penalized when the combination uses indirect targeting drugs or difficult-to-handle drugs (e.g., due to a patient's susceptibility to allergies, a patient's liver function, a patient's renal function, or the like). The score attributed may be a numerical value, as well as a qualitative factor. The score may also or instead be expressed in any suitable or useful level of granularity such as with discrete categories, or with a numerical score, alphabetic score/grade, or other quantitative indicator. For example, the score may be a range-bounded quantity (e.g., a score from 0-10 or 0-100); the score may also or instead be scaled. The formula used to determine the score may be adapted in regards to the application. One example will be to attribute a numerical score for each of the pairs {drug-target(s)}, depending of the spectrum of activity of the drug. Then, all {drug-target(s)} scores may be added to assess the final score of one combination.

The quantification of the combination's efficiency/toxicity balance may allow for progression through a fifth processing step which includes sorting the combinations of drugs by relevant criteria. The combination's score may be the primary criteria used for the combinations' sorting. The user may also choose, e.g., via the web interface, an additional sorting criteria such as the number of drugs used, the number of targets assessed, the number of targets missed, the presence of acceptable targeting redundancies, or the presence of pharmacological class redundancies.

The sixth and last processing step may include displaying an optimized list of therapeutic options for one patient. Optimized therapeutic options may then be sent to the interactive web interface.

Figure 5B:
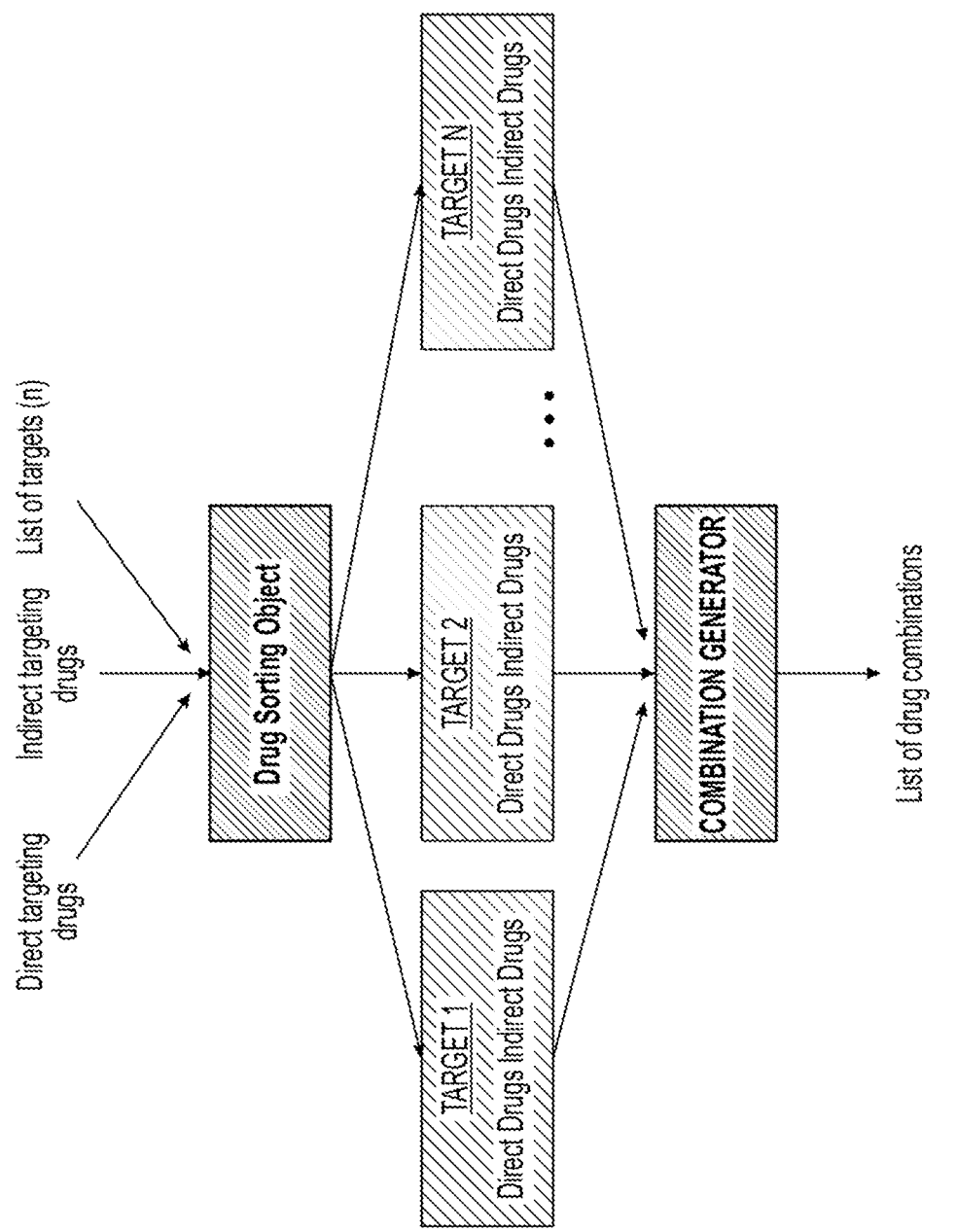
FIG. 5B illustrates a first type of combination generator.

FIG. 5B illustrates a first type of combination generator, e.g., used in the combining step of Module 3. Specifically, the figure shows a functional block diagram of an implementation of the combinatory module. The figure shows a drug group sorter that may use a list of all available directly-targeting drugs, a list of all indirectly-targeting drugs, and a list of all actionable targets as inputs. The drug group sorter may sort all drugs into different target containers. Each target container may be comprised of a list of drugs that directly act against said target and a separate list of drugs that indirectly act against said target. The combination generator may iterate through each target container and select one drug-target pair from each container from either the direct or indirect category. The combination generator may select drugs from each target container so that every possible combination of drug-target pairs covering all targets is created. Each combination of drugs may be passed to the combination scoring function. This method may include the advantage of ensuring complete coverage of all inputted genes by each drug combination, at the cost of potentially increased toxicity due to the higher amounts of drugs being used.

Figure 5C:
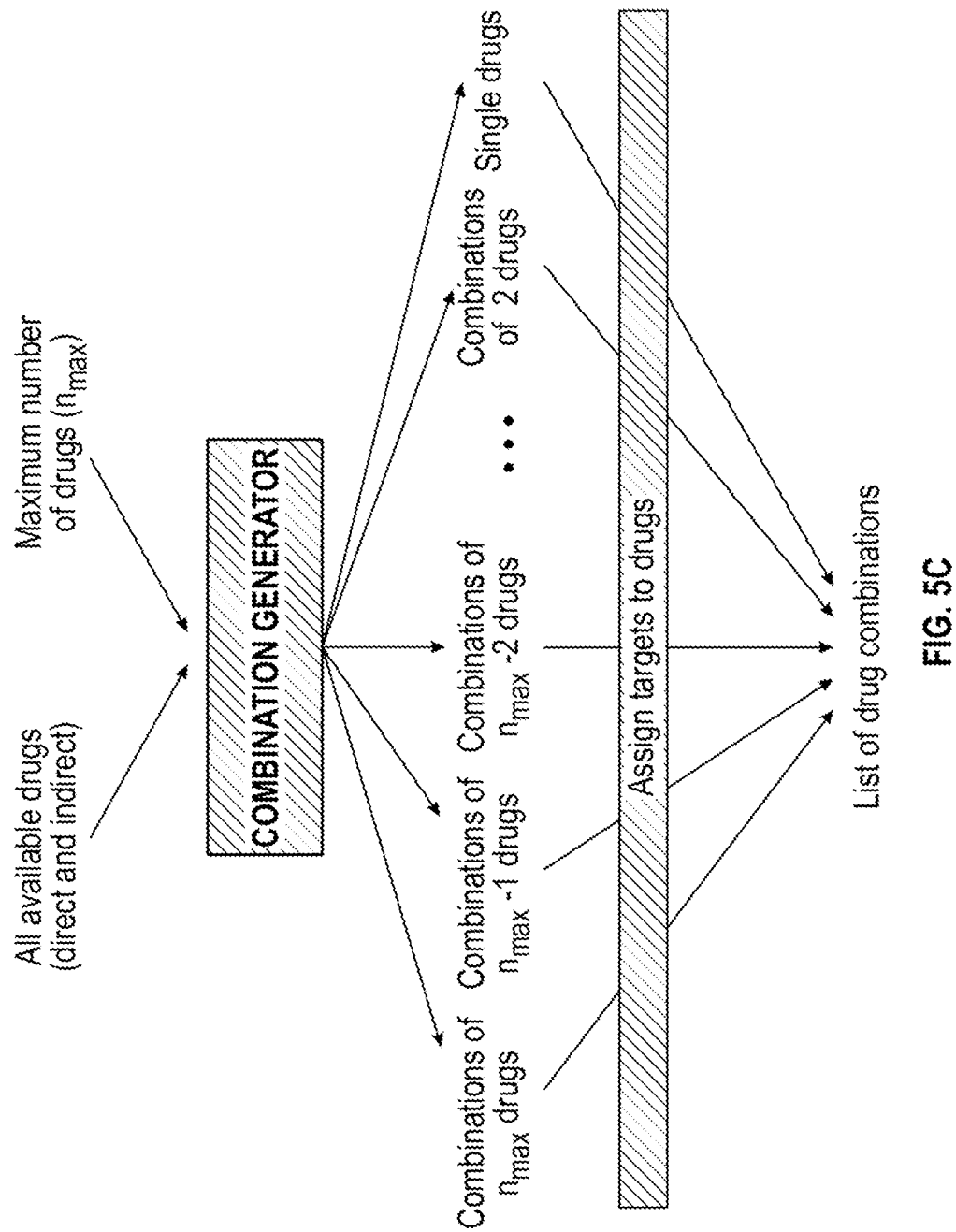
FIG. 5C illustrates a second type of combination generator.

FIG. 5C illustrates a second type of combination generator, e.g., used in the combining step of Module 3. Specifically, the figure shows a functional block diagram of an alternate implementation of the combinatory module. The figure shows a combination generating object that uses a list of all available drugs and a user-set maximum number of drugs as inputs. The combination generator may generate all possible combinations of up to and including the maximum number of drugs. Each combination of drugs may be matched to the drugs' targets and this data may be passed to the combination scoring function. Since this system may only generate combinations with a limited number of drugs based on a user-defined maximum, it can have the advantage of suggesting combinations with reduced toxicity, at the cost of potentially less complete coverage of the inputted genes.

Figure 5D:
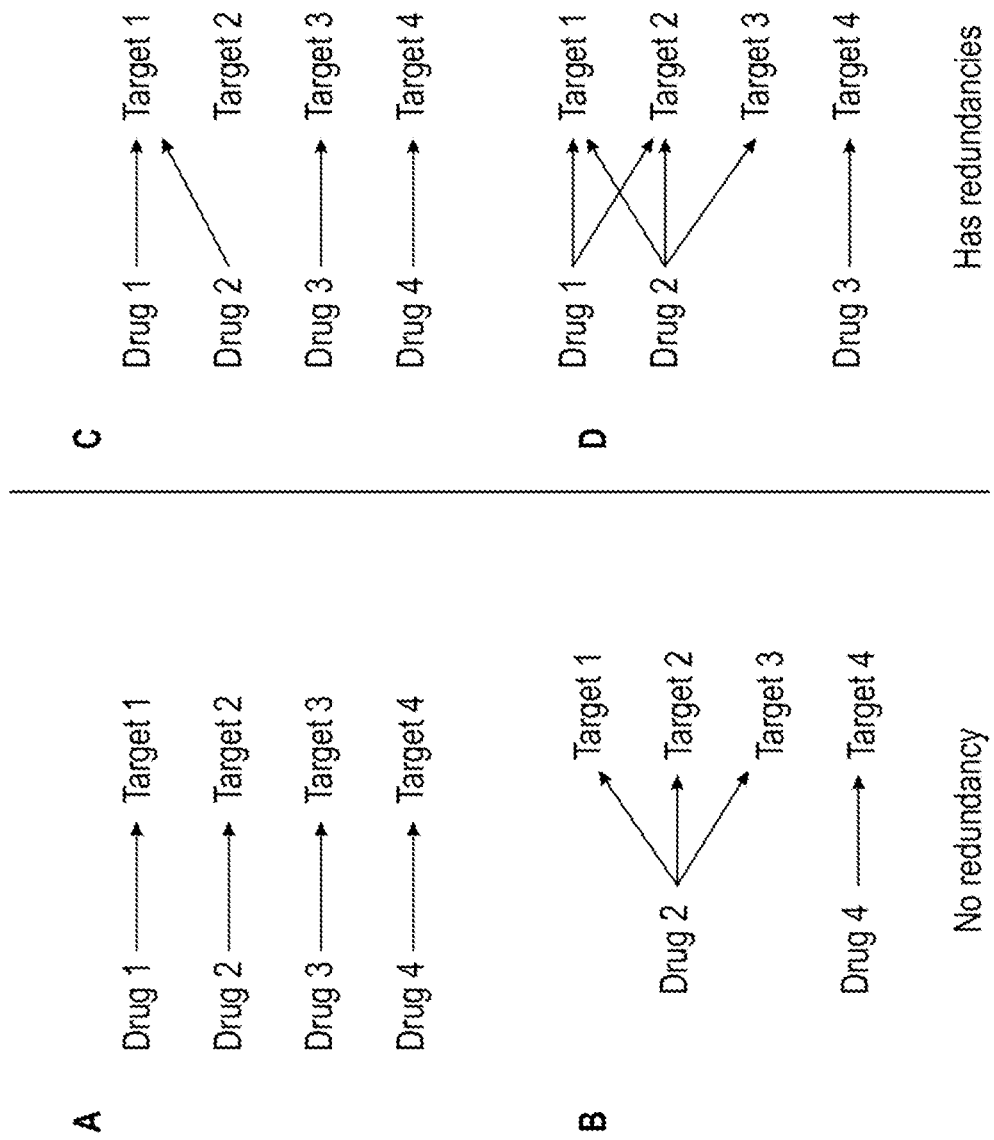
FIG. 5D illustrates filtering by targeting redundancies.

FIG. 5D illustrates filtering by targeting redundancies, e.g., a technique that can be used in the filtering step of Module 3. Specifically, the figure shows examples of outputted combinations with and without redundancies, where a redundancy is defined as multiple drugs acting on the same target in any form, directly or indirectly. In the figure, combinations 'A' and 'B' have no redundancies since each drug acts on a unique set of targets. Combinations 'C' and 'D' have redundancies since several drugs act on the same set of targets (Drugs 1 and 2 act on Target 1 in combination 'C'). Combination 'D' may also be considered as acceptable since Drug 2 additionally acts on Target 3, even though Targets 1 and 2 are redundantly targeted by Drugs 1 and 2.

Figure 5E:
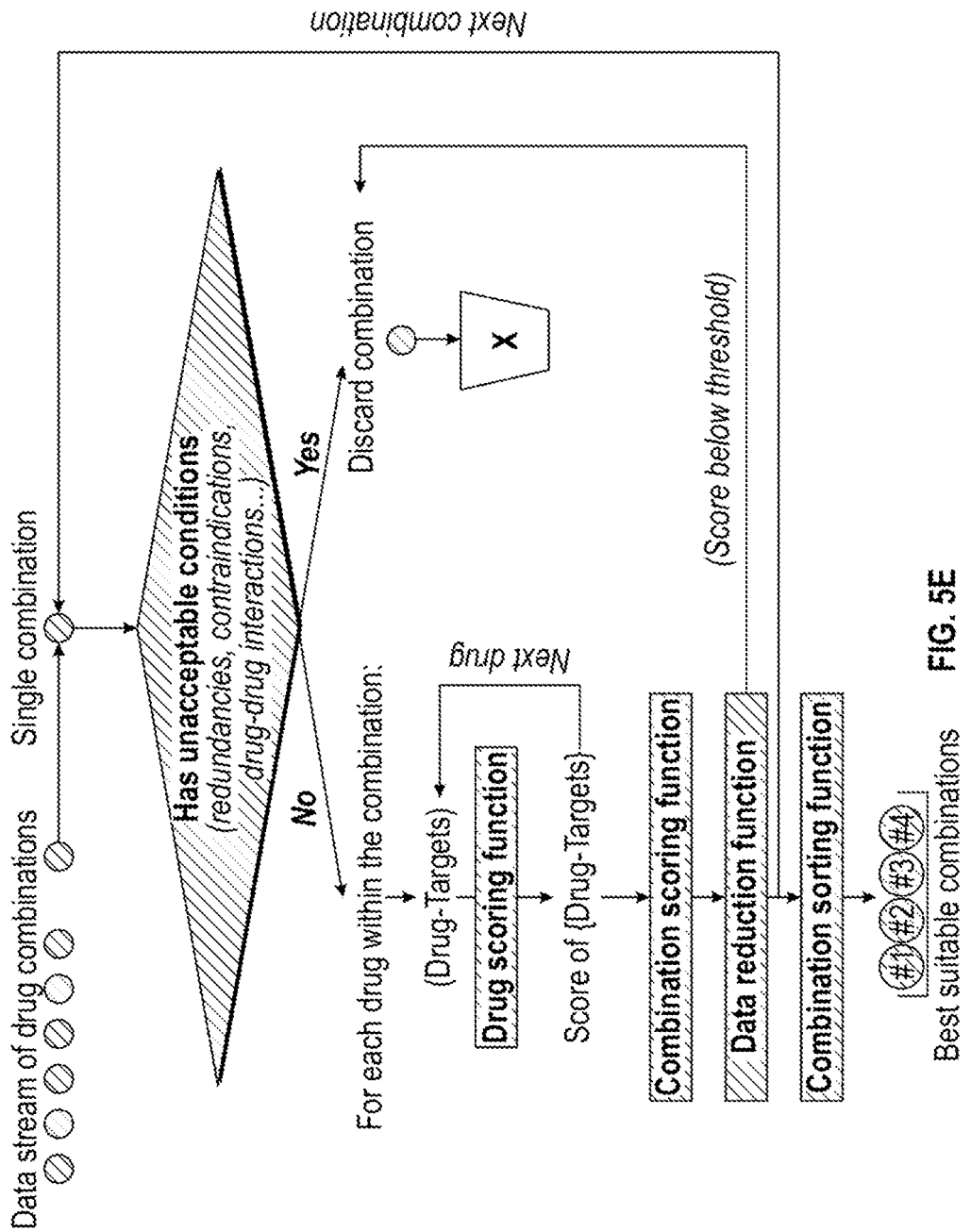
FIG. 5E illustrates filtering, scoring, and sorting.

FIG. 5E illustrates filtering, scoring, and sorting. The techniques shown in this figure may be used in Module 3 as described herein, as a post-combinatorics data stream. Specifically, the figure shows a functional block diagram of a drug combination scoring module, which may be implemented after the filtering processing step. An inputted list of drug combinations may be iterated through, which then yields lists of drug-target pairs one at a time. This list of drug-target pairs may be checked for targeting redundancies. If unacceptable conditions are detected, then the combination may be discarded with no further processing. If acceptable conditions are detected, then the combination may be sent to the scoring processing step. For each drug-target pair within the combination, the scoring function may determine a numerical score based on the biochemical activity of the drug upon its target. Additional advantage or penalization factors may apply. After iterating through the entire combination, the overall combination score may be passed to the data reduction process, which determines whether or not to save the drug combination in the drug combination storage database, depending on whether or not the score meets or exceeds a calculated threshold value. Combinations that do not meet or exceed a calculated threshold value may be discarded with no further processing. The combination scores may be used by the following module to sort each combination relative to one another within the same case.

Figure 6:
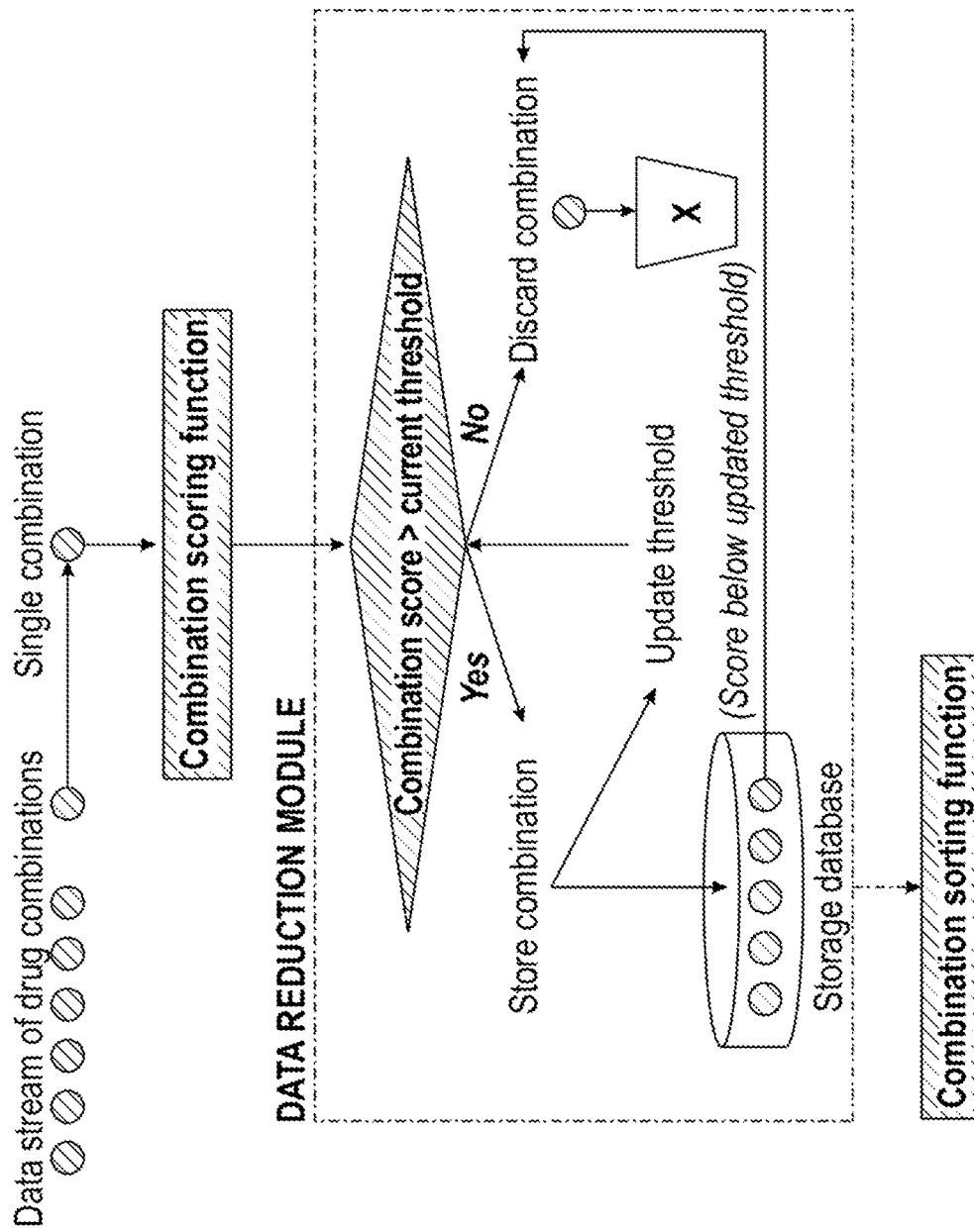
FIG. 6 illustrates a data reduction process.

FIG. 6 illustrates a data reduction process.

The number of drug combinations generated by the decision-making machine may be directly linked to the number of biomarkers presented by a patient and the number of available drugs which target said biomarkers. With the widespread development of high-throughput molecular profiling methods, the amount of both of these tend to increase exponentially, exceeding the calculation and storage capacities of most hardware resources (e.g., RAM memory, disk space on hard drive, and the like) of computer systems that store the system and analyze the data in a timely manner. For example, an ordinary profile presenting ten different biomarkers, each of them being actionable through five different drugs, will theoretically generate a list of 15,258,775 combinations using between 1 and 10 drugs.

To avoid extensive calculation times, the decision-making machine may use a self-optimized filtering system to selectively save elements of a data stream (in this case, the list of all combinations) without any prior in-depth knowledge of the stream's contents (in this case, the detailed combinations and the combination's scores). The filter module may accept individual drug combinations as data points from the overall system as the overall system generates all possible drug combinations in a continuous arbitrarily long data stream. After receiving the first combination, the module may score the combination using a scoring function and compare it to a threshold score. A threshold may be arbitrarily chosen before implementation of the system and may be, for example, the median of combination's score (corresponding to the patient studied) already saved at this particular time. If the combination's score meets or exceeds the threshold score's value, the module's update process may save the combination to a working database and update the threshold score in consequence (re-median function). In addition, if the number of stored combinations is greater than a certain limit, the module may delete previously saved combinations whose score(s) are the lowest, in order to respect the limit of storage previously defined. If the combination's score is below the threshold value, it may discard the combination with no further processing. This process may be repeated for every combination fed to the filter module. The fact that only combinations whose scores meet or exceed the threshold may be used to change the threshold means that the threshold score may be constantly increasing. The deletion of points that cannot meet the increasing threshold at every iteration can save disk space and future computational effort because it limits the amount of drug combinations to be saved to only the optimal ones for the patient, fulfilling the overall goal of the personalized medicine decision support system (as shown in the figure).

Specifically, the FIG. 6 shows a data reduction module of the decision-making machine that generates various, innumerable amounts of drug combinations depending on the patient-specific genetic aberration data input. Each drug combination may be numerically scored based on its clinical and biochemical efficiency as well as other parameters such as regulatory data, drug-drug interactions, and patient medical history. The data reduction module may accept individual drug combinations (data points) from the overall system as the overall system generates all possible drug combinations in a continuous arbitrarily long data stream. After receiving the first combination, the module may compare the score of said combination to a threshold score (e.g. median of combination already saved). If the combination's score meets or exceeds the threshold score's value, the module may save the combination to an output database and updates the current threshold score. In addition, the module may delete previously saved combinations from the database whose score is below the current threshold score. If the combination's score is below the threshold value, it may discard the combination with no further processing. This process may be repeated for every combination fed to the filter module. The deletion of points that cannot meet the increasing threshold at every iteration can save disk space and future computational effort, as well as limits the number of combination to be saved to only the optimal ones.

A supervised learning machine will now be discussed, such as that used in Module 4 of a system similar to that shown in FIG. 1A.

The results provided by a decision-making machine may be constantly optimized by at least two distinct supervised-learning methods using either a retrospective database of results obtained in patients (e.g., clinical response database), or a database of prospective results obtained on cell-lines or animal models (e.g., in vitro/in vivo response database). A supervised-learning machine resulting of the implementation of these two methods may optimize results generated by the decision-making machine, by fine-tuning and/or re-sorting the list of suitable combinations of drugs, thereby improving the clinical reliability and relevance of the results provided.

A supervised learning technique using retrospective clinical outcomes will now be discussed. An implementation of a supervised-learning module is based on the accumulation of treatment regimens and outcomes records, retrospectively collected after expert review (e.g., published clinical trials) or after a system's users' feedback. This data may be stored in a constantly updated knowledge database, also called clinical outcome database (see FIG. 7A and FIG. 7B).

Figure 7A:
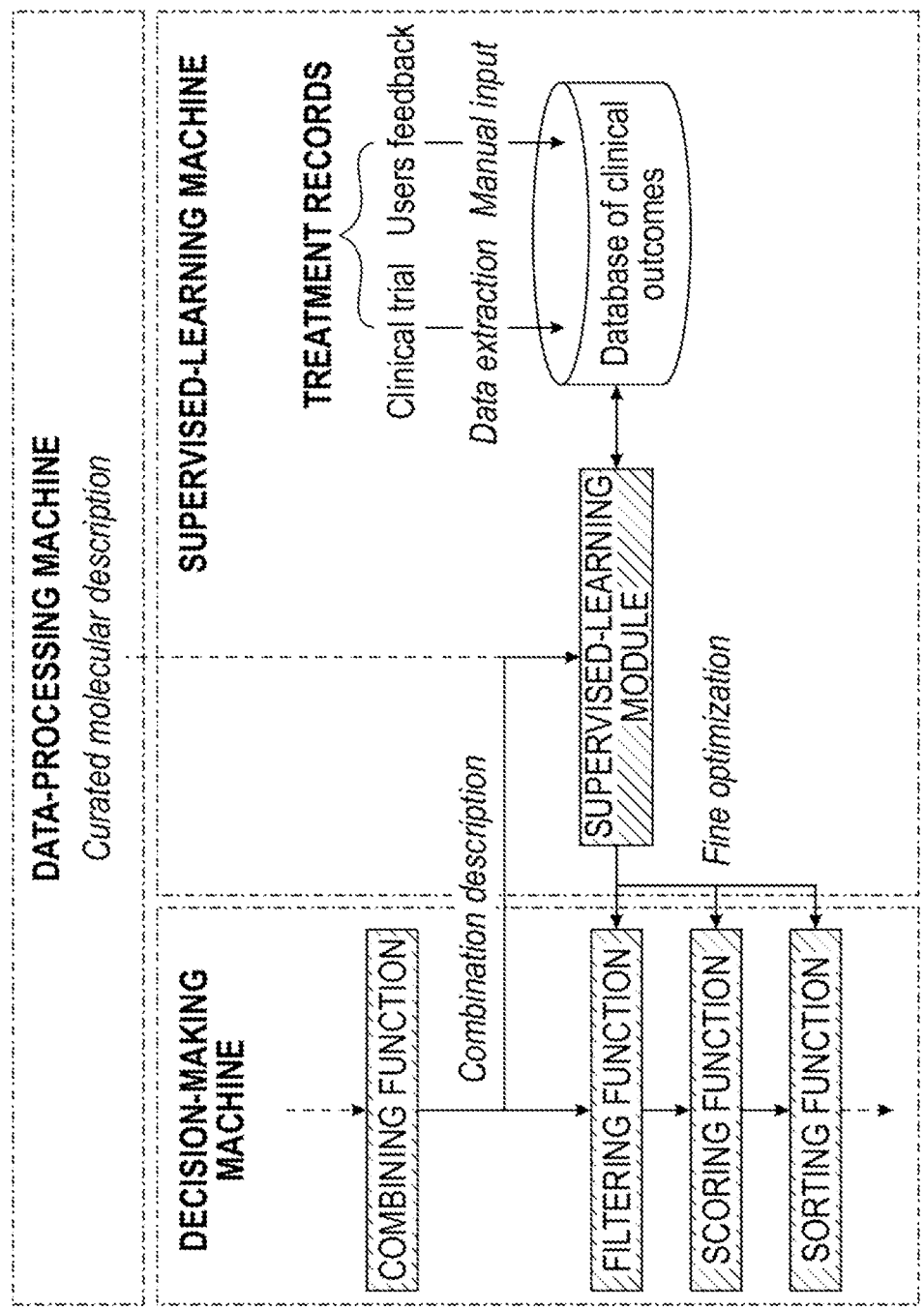
FIG. 7A illustrates a decision-making machine and supervised-learning machine interaction.

FIG. 7A illustrates a decision-making machine and supervised-learning machine interaction. Specifically, the figure illustrates how the supervised-learning machine may interact with the decision-making machine. Original decision-making machine combinatorics results may be transmitted to the supervised-learning machine and associated with the initial curated molecular description from the data-processing machine. The supervised-learning module may query a database of already-known clinical outcomes to find similar cases (e.g., using a similarity function) and compute a modifying factor related to the different outcomes observed in such cases. The modifying factor may be used to optimize the filtering, scoring, and/or sorting processes of the decision-making machine. The knowledge database may include data collected retrospectively by curation of published clinical trials and/or review of outcomes observed by the user in patients after using the decision-support system's results.

The clinical outcome knowledge database may be controlled by automated and manual input. Each treatment record may include a diagnosis, a set of biomarkers, a set of drugs prescribed (and their conditions of dispensation), and an outcome obtained in a case after treatment by said drugs (see FIG. 7B). For cancer cases, the outcome may be defined using the RECIST (Response Evaluation Criteria in Solid Tumors) criteria such as "Complete Response" (CR), "Partial Response" (PR), "Stable Disease" (SD), or "Progressive Disease" (PD). The duration of the observation may also be indicated (e.g., "Stable disease for more than 6 months"). Additional secondary information, whether clinical (e.g., age at diagnosis, gender, comorbidities, and the like) or technical (e.g., date of submission, user's identification, curator's identification, and the like) may also be stored.

Figure 7B:
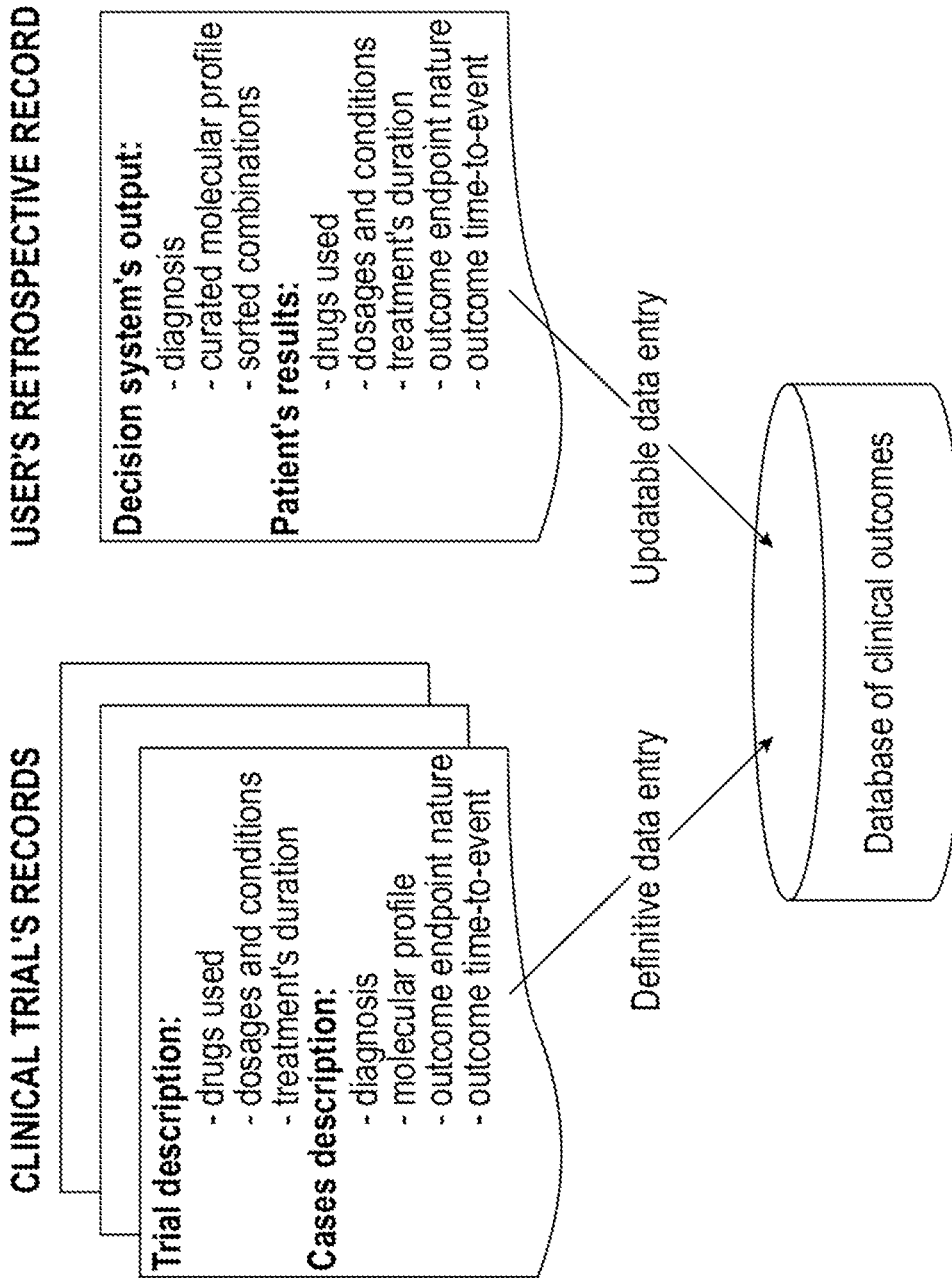
FIG. 7B illustrates curation of treatment records.

FIG. 7B illustrates curation of treatment records. Specifically, the figure illustrates an example of the origin of the primary key data that may be used to build the clinical outcome database. The data used may be results of published clinical trials or system's user retrospective feedback. The description of each relevant case studied in the clinical trial may be retrieved (e.g., diagnosis, molecular profile, and outcome description) and associated with the clinical trial protocol information (e.g., drugs studied, dosage, and duration of treatment description). In an aspect, once entered in the database, clinical trial cases' reports can't be modified. Decision support system's users can agree to participate to the continuous improvement of the system by providing regular patient's follow-ups. In this case, the information corresponds to the patient's system output stored in the interface database (diagnosis, molecular profile, and best combinations description), associated with data regarding the regimen chosen by the clinician (drugs, dosage, and duration description) and data regarding the outcome observed in the patient, reported in a timely manner. Entries corresponding to users' feedback may be updated at any moment, depending on the patient's medical condition.

Figure 7C:
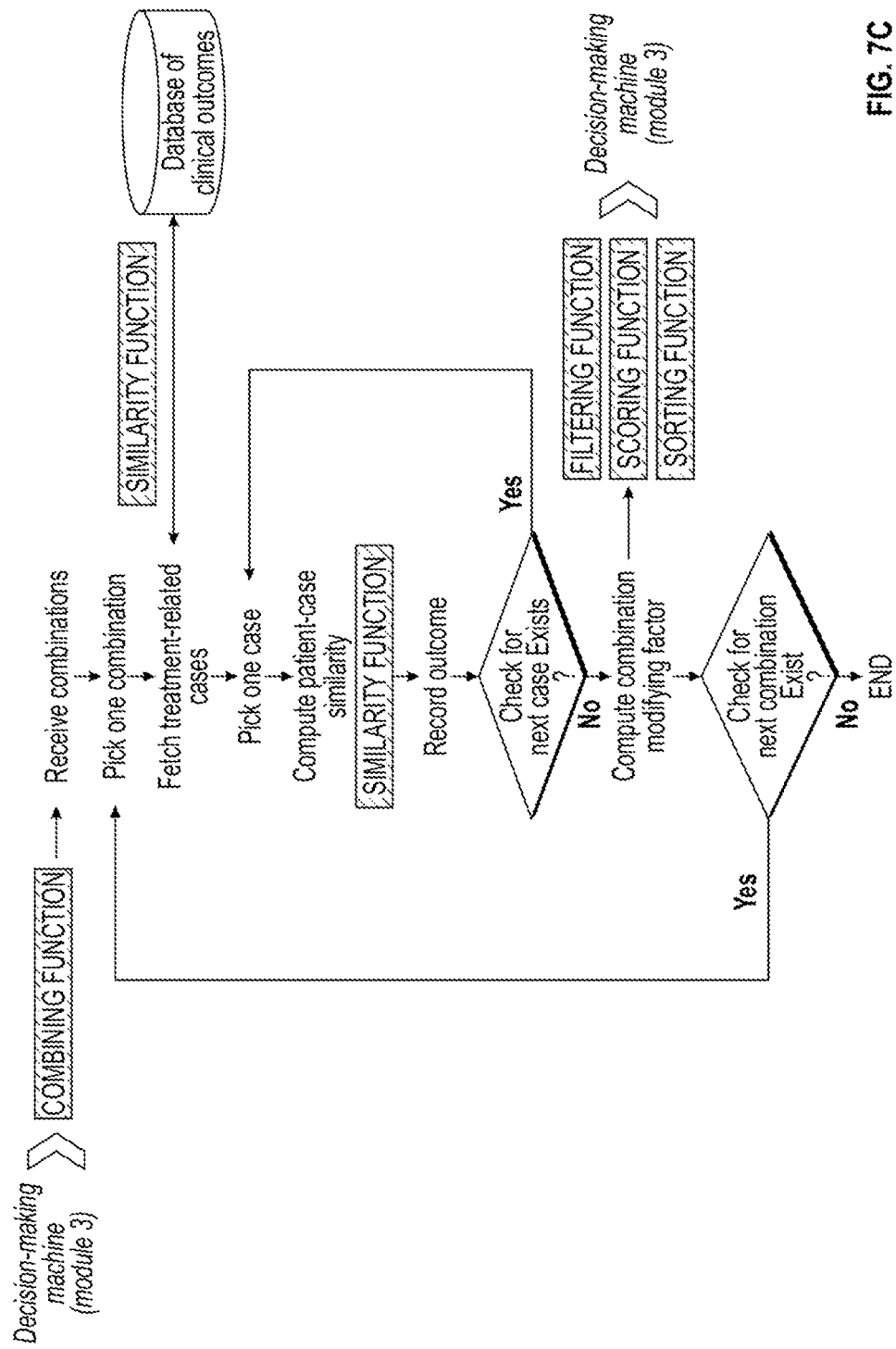
FIG. 7C illustrates a supervised-learning module's process.

FIG. 7C illustrates a supervised-learning module's process.

In this approach, the predefined algorithm may compare each combination generated for one patient to relatively similar cases that are known and found in the clinical response database and defined as {molecular profile-treatment regimen-outcome} systems. In an aspect, only clinical outcome records presenting a minimal degree of similarity are considered. The outcomes observed for these cases may be the primary criteria used to optimize the results obtained by the computational-only method. The algorithm may provide a modifying factor, based on the degree of similarity between the {patient-combination} system actually studied and all corresponding {molecular profile-treatment regimen-outcome} systems stored. This factor can be used to directly or indirectly affect the filtering, scoring and/or sorting processing steps of the decision-making machine (see FIGS. 7A and 7C), and thus lead to a re-ranking of the initial list of combinations.

FIG. 7C shows a process of producing new results by re-filtering, re-scoring, or re-sorting an original list of combinations, in accordance with published and expert knowledge from the clinical outcome database. The supervised-learning module may use a similarity function to retrieve comparable cases from the database, based on the molecular profiles and treatment options descriptions. This similarity may be quantified by a numerical factor. Each comparable case from the database, represented by its degree of similarity and its outcome, may be kept to compute the combination's modifying factor, which in turn may be apply to the initial ranking of said combination. All combinations produced by the decision-making machine may be evaluated by the supervised-learning machine.

Figure 7D:
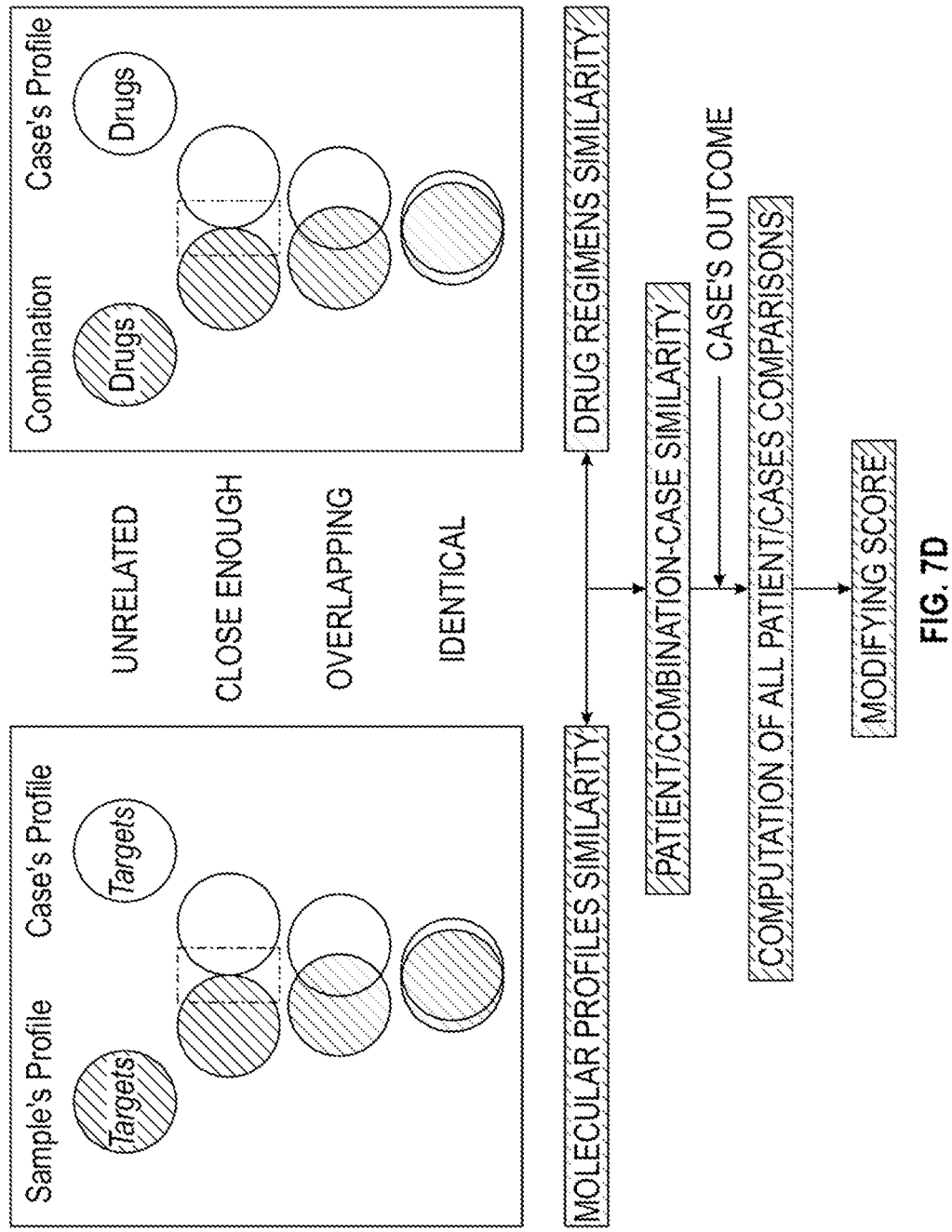
FIG. 7D illustrates a similarity function.

FIG. 7D illustrates a similarity function.

The overall degree of similarity between the {patient-combination} system studied and each case stored may be the result of at least two types of similarities: the molecular profile similarity and the treatment regimen similarity factors as shown in the figure.

First, the molecular biomarkers found in both the patient and the stored cases may be considered. The degree of molecular similarity may be defined by the exact same sets of identical biomarkers, a partial overlap between the profiles observed, and/or an absence of overlapping but a set of biomarkers that can be considered as "close enough" at the biological level as shown in the figure. For example, molecular biomarkers located within the same family of genes or the same signaling pathway may be considered as "close enough" to each other, as these alterations may induce the same biological effects (see FIG. 7E). All single biomarker comparisons existing between the patient studied and the case observed may be aggregated to define a unique molecular profile similarity factor.

Second, the set of drugs proposed in the combination and the therapeutic regimen actually tried by the cases may be compared. The degree of treatment similarity may be defined by the same sets of identical drugs, a partial overlap between the drugs, and/or an absence of overlap along with a set of drugs that can be considered as "close enough" at the pharmacological level (see FIG. 7D). For example, drugs belonging to the same pharmacological class or targeting the same family of molecules may be considered as "close enough" to each other, as these drugs may present the same spectrum of activity (see FIG. 7E). All single drug comparisons existing between the combination studied and the therapy regimen's case observed may be aggregated to define a unique treatment regimen similarity factor.

The degrees of similarity between molecular or therapeutic elements may take the form of a quantitative (e.g., obtained by distance metric function) or a qualitative factors. One may compute such numerical distance by using a hierarchical approach. The distance between two elements may be defined as the shortest path on a weighted graph (e.g., tree) representing the arbitrary relationships between elements. In general, the distance between two consecutive nodes may be one by default, but this value may be adjusted for specific needs. The comparison between similar elements may provide a distance of zero. Two elements not presenting any common parent node may be considered as unrelated. The distances values obtained for each comparison may be used within the learning-machine module.

FIG. 7D shows how the similarity between the patient/combination actually studied and the cases found in the clinical outcome database may be evaluated. For one combination, molecular profile and therapeutic regimen may be compared to all cases from the database. Some cases may show an identity, an overlapping, or a close relationship of targets and/or drugs compare to the combination of interest. The degree of similarity may be a quantitative or a qualitative factor. A global factor of similarity resulting of both molecular and therapeutic similarity may be defined and associated with an observed outcome. All cases-related comparisons may be used to compute a modifying factor, allowing the re-ordering of said combination within the decision-making machine.

Figure 7E:
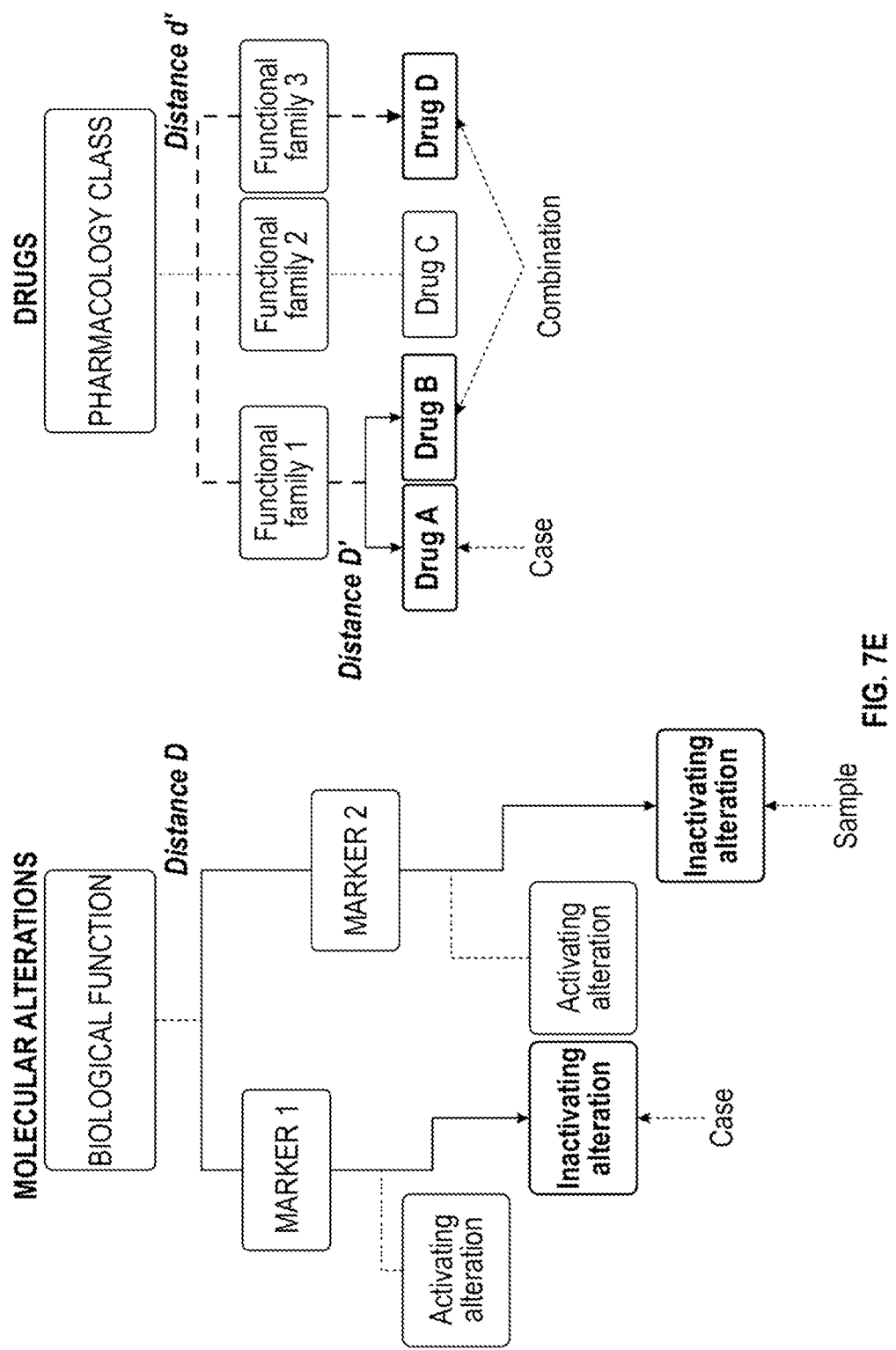
FIG. 7E illustrates an evaluation of a similarity between non-identical elements.

FIG. 7E illustrates an evaluation of a similarity between non-identical elements. The figure represents examples of systems that may be used to evaluate the closeness between non-identical but related molecular alterations and drugs. The distances between common targets and common drugs can be defined using a hierarchical approach. The distance between two elements may be defined as the shortest path on the weighted graph (tree). In this example, the system generated the combination of Drug B and Drug C for a sample presenting an inactive alteration of marker 2. The supervised-learning module may estimate the distance between this result and a known case presenting an inactive alteration of marker 1 and treated by the Drug A. At the molecular level, the distance between the sample and the case is Distance D, whereas the distance between the drug regimens is a computation of Distance D' and Distance d'. In general, the distance between two nodes on the tree is one by default, but an expert can provide an adjustment by increasing or decreasing the value. Distances of zero generally correspond to the exact same element (alteration or drug). For two elements without any common parent node, the distance may not be calculated and the elements are considered unrelated.

A supervised learning method using prospective in vitro or in vivo experiments will now be discussed. This supervised-learning method may be based on the assessment of drug combination efficiency on experimental models, such as cell-lines or animal models. These models may be genome-edited (e.g., using methods such as CRISPR/Cas9 for cell-lines or knock-out/knock-in engineering for animal models) in order to mimic the molecular profile found in the sample (and provided by a data-processing machine). The models may then be used in an in vitro drug-response assay (e.g., in the case of cell-lines) or in vivo drug response experiments (e.g., in the case of animal studies), using regimens of drugs selected from the list of combinations generated by the decision-making machine. The activity of each drug regimen may be assessed by different techniques (e.g., proliferation, survival, or specific assays) and may be compared to non-treated models and/or standard therapeutic strategies commonly used to treat the disease presented by the patient. Use of cellular and/or animal models may also allow the definition of suitable dosages, by testing several ratios of drugs. Results of these experiments may be sent and stored in a knowledge database. The database of in vitro or in vivo experiments results may be used by the supervised-learning machine to tune the functions of the decision-making machine and re-order combinations in regards of the results obtained (see FIG. 8). Results concerning the adaptation of dosage may also be provided as a recommendation to clinicians.

Figure 8:
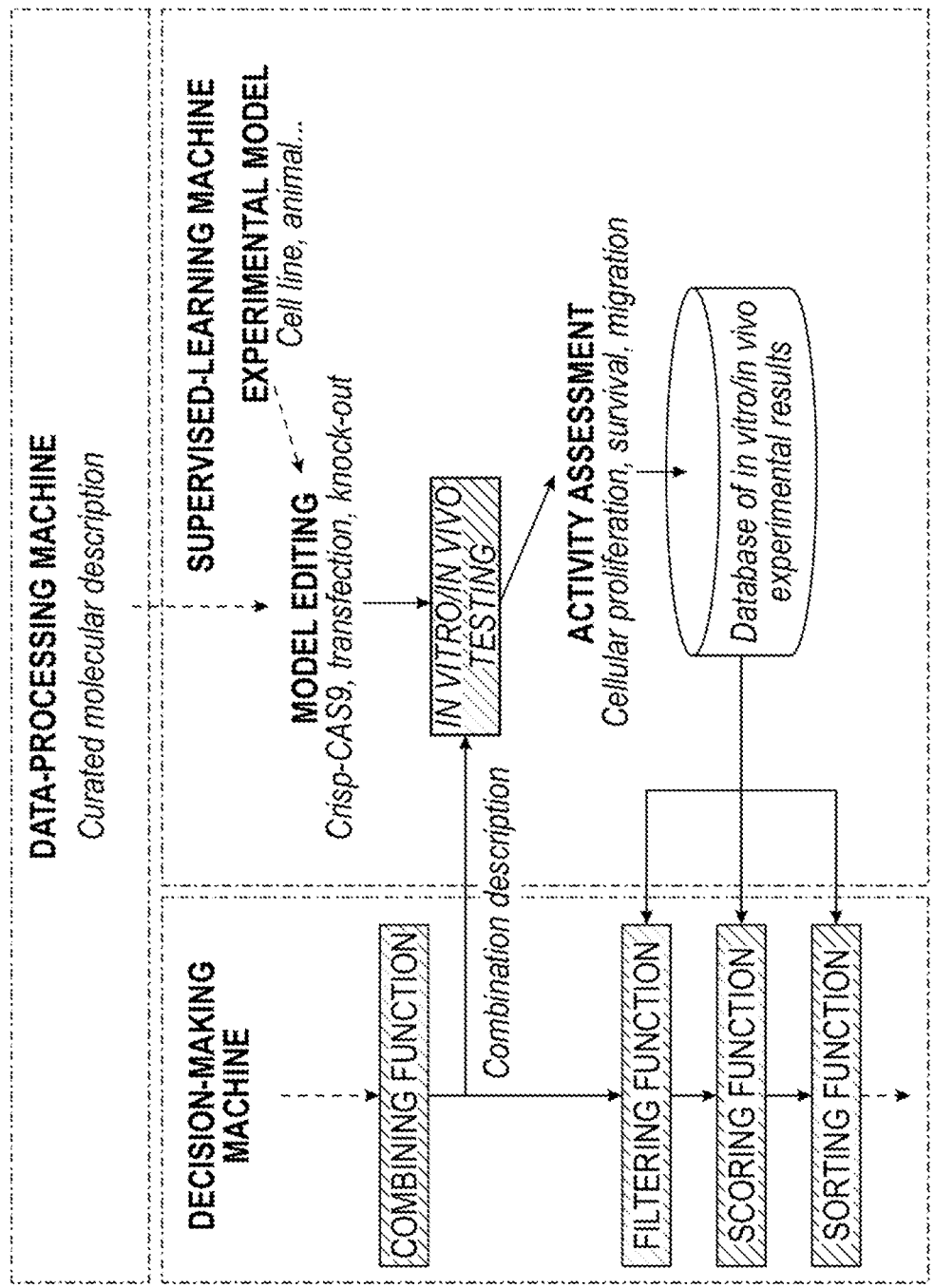
FIG. 8 illustrates a decision-making machine and supervised-learning machine interaction.

FIG. 8 illustrates a decision-making machine and supervised-learning machine interaction. The figure illustrates an example of how the supervised-learning machine interacts with the decision-making machine. Information on the initial molecular alterations present in the sample may be used to specifically edit experimental models such as cell-line or animal models. This may result in models presenting a similar molecular profile which mimics that of the patient. These edited models may then be used in an in vitro or in vivo drug-response assay, using regimens of drugs selected from the list of combinations generated by the decision-making machine. The activity of each drug regimen may be assessed by different techniques and the results are sent to a dedicated database. This database may be used by the supervised-learning machine to tune the functions of the decision-making machine and re-order combinations in regards of the results obtained.

A web interface or results output will now be discussed, such as that used in Module 5 of a system similar to that shown in FIG. 1A.

The results generated by the decision-making program may be displayed in a designated location, e.g., on a web-interface that may be a separate page or a section of another existing page. The results to be displayed may include the user-inputted parameters used for calculation (including, e.g., clinical, demographic, and molecular information relating to the patient), the aberration effect determination results, and the suggested drug combinations as recommendations to the clinician (see FIG. 9A). Additionally, a printable report may be generated (see FIG. 9B).

In each individual drug combination, the clinician could also be recommended a specific dosage of each drug in the combination. This optimization of posology (dosage) may be determined by expert input, clinical observations, and in vitro/in vivo drug response experimentations.

The drug combinations outputted can be searched without altering their contents using a specialized search function. Users may request to see all combinations, or only to see combinations that fit criteria such as but not limited to: including certain drugs, excluding certain drugs, having no redundancies, having a certain number of FDA indicated drugs, and having a certain total number of drugs.

Figure 9A:
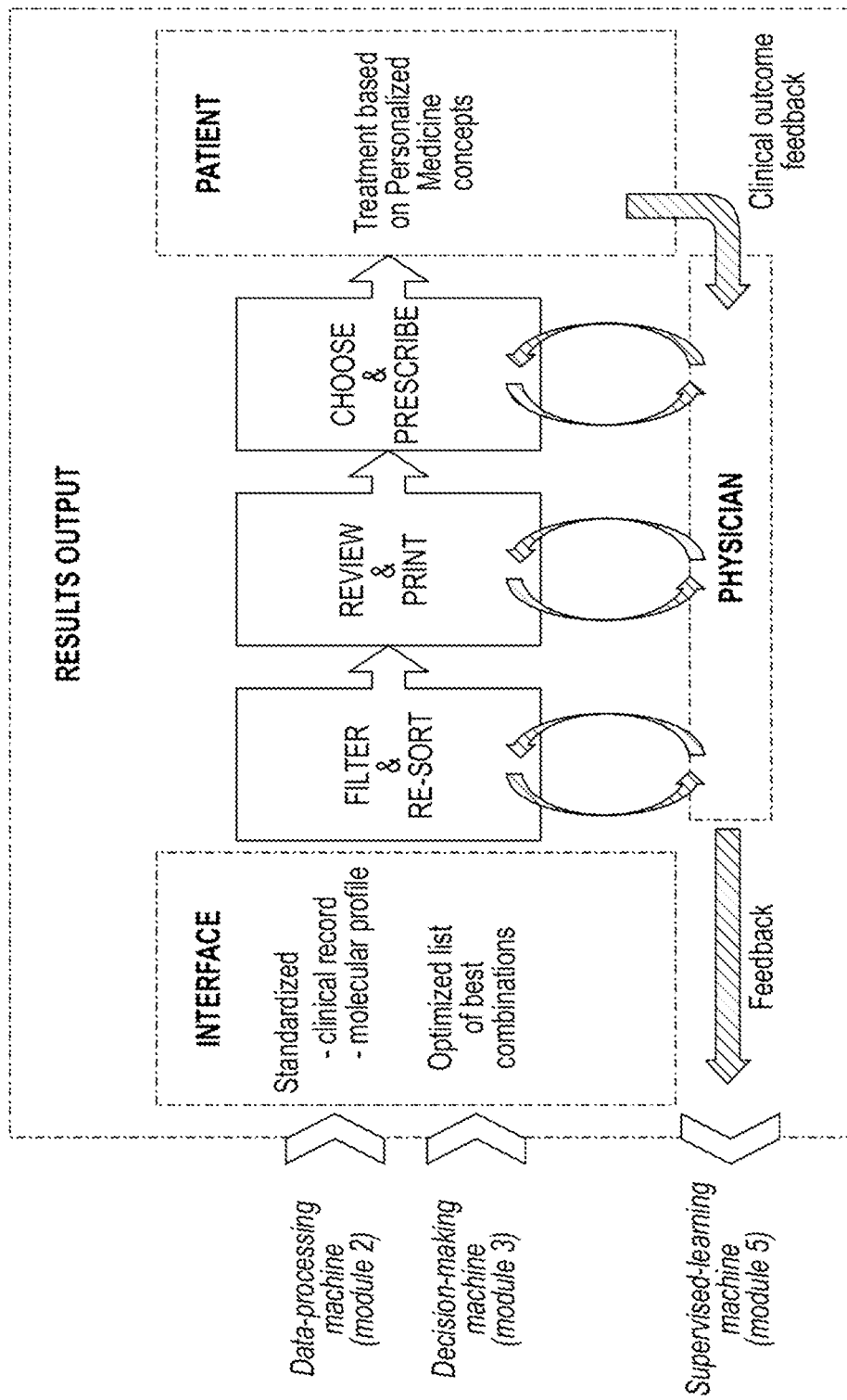
FIG. 9A illustrates results output.

FIG. 9A illustrates results output. The figure shows examples of the interactions between the user and the system's interface after completion of a computational job. The user may review the results generated by the decision-making machine, where the user is able to modify criteria used to filter and sort the optimized list of combinations of drugs. After reviewing, a comprehensive report based on user's preferences and selections may be printed. The user (if a physician) may select the therapy regimen to prescribe to his/her patient. After treatment, the physician may record and transmit to the interface the clinical outcome observed in his patient.

FIG. 9B illustrates an example of a report, e.g., a report generated by the user interface. The figure thus presents an example of a printable comprehensive report generated by the user-interface after review of the results and used as a recommendation tool for clinicians.

Several prophetic examples will now be described.

Example 1

A 62-year-old man diagnosed with a BCLC (Barcelona Clinic Liver Cancer) Stage B hepatocellular carcinoma (HCC) was initially treated with chemoembolization but, nevertheless, developed a metastatic disease. Despite treatment with sorafenib (NEXAVAR®), the disease continued to progress, at which time his physician ordered a molecular profiling of the cell-free DNA (cfDNA) extracted from a blood sample. The cfDNA profile shown the following genomic alterations: (i) "CDKN2A R80*" in 0.55% of all cfDNA extracted, and (ii) "CTNNB1 G34V" in 1.35% of all cfDNA extracted. The physician enter these two alterations, the diagnosis, and the clinical description in a decision-support system via the web-interface as described herein, and ordered the computation of all beneficial personalized combinations using two drugs or less by clicking on a "calculate combination" tab. The physician would like, if possible, to use drugs approved by the U.S. Food and Drug Administration (FDA), regardless of the pathology, and to access the functional effect of alterations database level 2 or 3 (high level of confidence). The physician indicates these criteria by selecting the corresponding option on the screen provided in the system.

Figure 10:
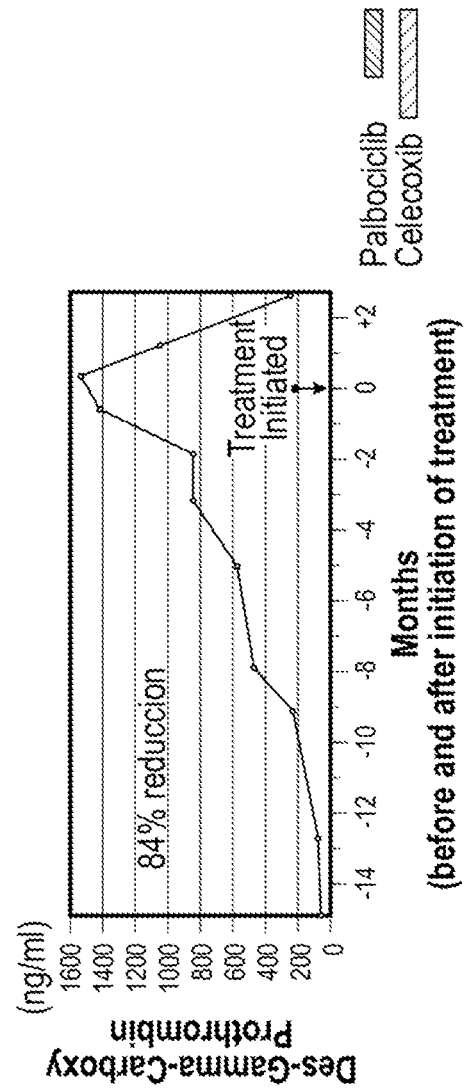
FIG. 10 illustrates a first prophetic example.

The data is then entered by the physician is then curated by the data-processing machine (see 'A' in FIG. 10).

The diagnosis inputted ("BCLC Stage B HCC") is translated in "Hepatocellular Carcinoma." The data-processing machine does not send this information to the decision-making machine, as the disease-indicated criteria is not mandated by the physician. This information is directly sent back to the user-interface.

The first alteration ("CDKN2A R80*") is translated in "p16INK4 p.Arg80*". This mutation entry exists in the database of functional effect of alterations. It corresponds to a nonsense mutation of the gene CDKN2A, leading to the truncation of the protein p16INK4 after the amino-acid 80, when the canonical protein should present a total of 156 amino-acids. The altered protein lacks of the third and fourth ankyrin-CDK4-binding repeat, and the natural function of regulation of the cell-cycle by CDK4-binding is lost. This alteration has been studied by in-depth computer structure-activity modeling, is considered as oncogenic, and is sent to the decision-making machine for combinations' computation.

The second alteration ("CTNNB1 G34V") is translated in "CTNNB1 p.Gly34Val". This missense mutation disrupts the phosphorylation of the β-catenin protein, leading to the constitutive activation of the Wnt (Wingless-Type) signaling pathway. This alteration has been studied by in-depth computer structure-activity modeling, is considered as oncogenic, and is sent to the decision-making machine for combinations' computation.

The decision-making machine then considers three available drugs suitable for the molecular profile entered.

Drug 1: palbociclib (IBRANCE®), a CDK4/CDK6 inhibitor approved by the FDA for metastatic breast cancer, which may be used to indirectly counteract the p16INK4 alteration.

Drug 2: sulindac (CLINORIL®), a non-steroidal anti-inflammatory drug (NSAID) approved by the FDA for various acute or chronic inflammatory states, which may be used to indirectly counteract the β-catenin alteration (by acting on COX-1 and COX-2 enzymes, effectors of the Wnt signaling pathway).

Drug 3: celecoxib (CELEBREX®), a COX-2 selective NSAID approved by the FDA for various acute or chronic inflammatory states, which may be used to indirectly counteract the β-catenin.

The decision-making machine initially generated a list of six different combinations using one or two drugs, but one combination was excluded by the targeting redundancy filter (the combination formed by the association of sulindac and celecoxib, both targeting the β-catenin alteration). After scoring and sorting of the five remaining combinations (see 'B' in FIG. 10), the best combination suggested was the combination [palbociclib+celecoxib].

Thus, the patient was started on a combination therapy treatment of palbociclib and celecoxib. Initially, the patient initiated celecoxib 200 mg twice a day. After 4 weeks, the level of des-gamma-carboxyprothrombin (DCP), a non-functional prothrombin which is generally regarded as a HCC biomarker, declined by 31% (from 1,520 to 1,046 ng/ml-normal: 0-7 ng/ml). Palbociclib was then initiated at a lowered dose (75 mg daily). Over the next 4 weeks, the level of DCP further declined to 242, an 84% decline from the baseline (see 'C' in FIG. 10). The tumor biomarker alpha-fetoprotein (AFP) was normal at baseline and thus was not further evaluated.

Six months later, the physician logs in to the system via the web-interface and completes the physician's feedback survey regarding the regimen prescribed to his patient and the outcome observed. In this particular case, the combination of a CDK4/6 to a COX-2 inhibitor to treat a tumor presenting both CDKN2A and CTNNB1 mutations showed a positive outcome classified as "complete response" following the RECIST criteria. The entry corresponding to this observation was created in the clinical outcome database and will then be used in order to optimize similar cases.

Two days later, another unrelated user logs-in into the system and orders the calculation of a therapy regimen for his patient, presenting a lung tumor where the genes CDK4 and CTNNB1 are mutated. The decision-making machine will generate a list of drug combinations where all solutions including a CDK4/6 inhibitor together with a COX inhibitor will see their score increased by a factor 2.

FIG. 10 illustrates the first prophetic example. In the figure, 'A' shows a summary of inputted data after curation by data-processing machine. In the figure, 'B' shows a list of combinations obtained as an output after filtering and sorting by the decision-making machine. In the figure, 'C' shows a patient's biological response after receiving a bi-therapy {celecoxib+palbociclib}. In this example, the plasmatic marker DCP (des-gamma-prothrombin) was reduced by 84% two months after treatment initiation.

Example 2

A 64-year-old woman diagnosed with hepatocellular carcinoma was initially treated with chemoembolization while awaiting a liver transplant. The patient received an orthotopic liver transplant and a year later was diagnosed with peritoneal carcinomatosis. She was treated with sorafenib (NEXAVAR®), added to her initial immunosuppressant treatment used after liver transplant (tacrolimus, PROGRAF®). DNA-sequencing analysis of explanted liver tumor was performed, and the next-generation sequencing (NGS) results showed a unique TP53 p.Arg273Cys mutation. A liquid biopsy, used to extract cell free DNA, revealed the following genomic alterations: a MET p.Tyr501Cys missense mutation, a TP53 p.Arg273Cys missense mutation, and a PTEN p.Leu139* nonsense mutation. All the mutations observed are considered as oncogenic and may be targeted directly or indirectly by at least one drug approved by the FDA.

The system as described herein recommended the regimen {cabozantinib-sirolimus} as one of the top scoring drug combinations. Firstly, the patient's treatment by tacrolimus was switched to sirolimus (RAPAMUNE®, mTOR inhibitor), as these two agents belong to the same pharmacology family. After 7 months, the patient was still evaluated as in progressive disease. Her physician decided to add cabozantinib (COMETRIQ®, MET inhibitor) to her regimen, even if this drug is not indicated in her pathology. Within one month, the level of tumor biomarker alpha fetoprotein (AFP) declined by 63% (8,320 ng/ml to 3,045 ng/ml-normal: 0-15 ng/ml]) (see FIG. 11).

Figure 11:
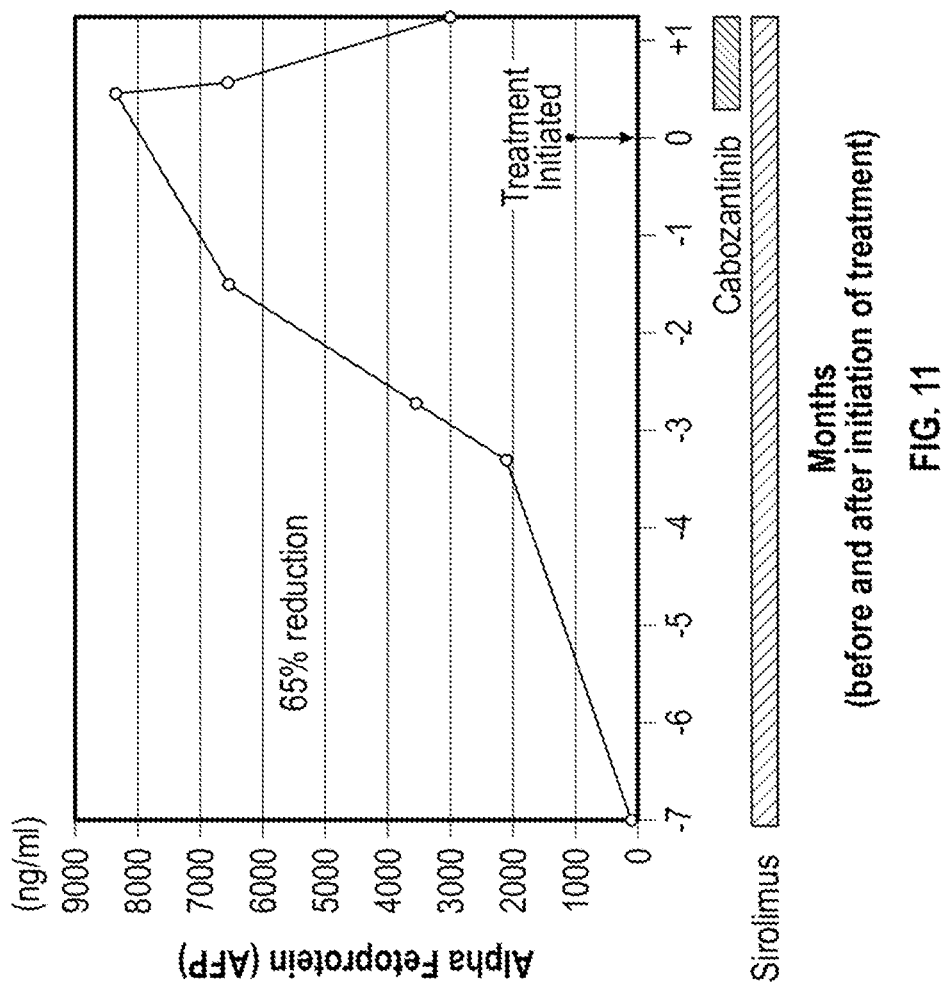
FIG. 11 illustrates a second prophetic example.

FIG. 11 illustrates the second prophetic example. The figure shows a patient's biological response after introduction of cabozantinib in her therapeutic regimen. The plasmatic marker AFP (alpha foetoprotein) was reduced by 65% after one month of treatment with a combined therapy of cabozantinib and sirolimus.

Example 3

This example involves a 57-year-old man who had surgery for several basal cell cancers. Nevertheless, the patient developed brain, bone, and liver metastases and was subsequently treated with the first and second generation of hedgehog inhibitors, vismodegib (ERIVEDGE®) and sonidegib (ODOMZO®), both FDA-approved for metastatic basal cell cancer. However, the patient was non-responsive to these therapies. In addition, gamma knife radiation was also performed for his brain metastases with a good response. He also received cisplatin (PLATINOL®) and paclitaxel (ABRAXANE®) with a short-lived response. Molecular analysis revealed a number of genomic aberrations, including an amplification of CD274 (programmed death ligand 1 PD-L1). The interaction of this ligand (PD-L1) with the programmed death receptor (PD-1), expressed on T and B cells, alters the function of these cells leading to inhibition of autoimmunity and anti-tumor immunity. In addition, ten other genomic alterations were noted. In this particular case, because of PD-L1 amplification and the large number of alterations, the system recommended to use an immunotherapy targeting PD-1.

The patient was started on nivolumab (OPDIVO®, anti-PD-1 antibody). After two months, scans showed remarkable partial remission and no toxicity was noted.

Matched combination therapy is likely to provide better outcomes for the cancer patient. However, in particular cases such as presented here, the system is able to prioritize non-conventional mono- or combination therapies, when this therapy has been proved as optimal in clinical studies.

Example 4

At one point, a previous version of the system described herein gave a score of 10 to the combination {trametinib-vemurafenib} used for a cancer patient with a tumor harboring a BRAF fusion and a MAP2K1 activating mutation. This combination is the third combination proposed within the list of best regimens.

After review of a clinical trial using the drugs {trametinib-dabrafenib} in patients (n=9) presenting a BRAF p.Val600Glu activating mutation, the supervised-learning machine allows the re-ordering of combinations, improving by a factor 1.8 the score of {trametinib-dabrafenib}, which becomes the best combination of the list.

To do so, the supervised-learning module computed the "molecular distance" between the tumor studied and the clinical trial's cases. This distance was equal to 0.2 between the BRAF alterations (same gene) and 1.8 between the MAP2K1 and the BRAF mutations. The molecular distance is the sum of these criteria and is equal to 2.

Then the supervised-learning module computed the "therapeutic distance" between the tumor studied and the clinical trial cases. This distance was equal to 0 for trametinib (same drug) and 0.1 between dabrafenib and vemurafenib (same functional family). The therapeutic distance is the sum of these criteria and is equal to 0.1.

The "closeness" ("C") between the patient and the trial's case may be calculated as follow:

$$(\text{molecular distance}+1) \times (\text{therapeutic distance}+1) = (2+1) \times (0.1+1) = 3.3$$

Among the trial's cases, one of them presented a complete response, four of them presented a partial response, three presented a stable disease, and one presented a progressive disease. Using these values, the system computed a factor of outcome prediction using the formula:

$$\frac{C \times (2N_{complete\ response} + N_{partial\ response} - N_{progressive\ disease})}{N\ cases} = \frac{3.3 \times (2 + 4 - 1)}{9} = 1.8$$

Thus, using this method, the results given by the decision-making machine are constantly optimized. This optimization is based on clinical observation in patients, after therapy by mono- or combination therapy. This optimization is dependent of the content of the clinical outcome database and thus will become more and more precise with time and system's usage.

Example 5

A physician order a combinatorics calculation for his patient, suffering from a ductal pancreatic adenocarcinoma, diagnosed at an early stage. The surgical resection of the tumor was performed and a molecular profile obtained by sequencing of a dedicated tumor sample showed a loss of the genes CDKN2A and CDKN2B, a mutation KRAS p.Gly12Val, and a mutation TP53 p.Arg175His. The surgery was a success and the patient is now considered as disease-free. Nevertheless, knowing the risk of recurrence of such a cancer, the physician orders the combination's calculation based on response observed on in vitro models experiments.

The SW-1990 pancreatic adenocarcinoma cell line, presenting a genotype close to the patient's tumor (CDKN2A/B loss and KRAS p.Gly12Asp), is chosen for the experiments. This cell line is edited using a CRISPR/Cas9 system, in order to present the third mutation (TP53 p.Arg175His).

The combination {palbociclib-trametinib-regorafenib}, presented by the decision-support system as one of the most performant regimen in this particular case, is tested on these cells. The results obtained on the cell proliferation and survival phenotypes are compared to the three agents considered separately, as well as to the standard of care for this pathology. The tri-therapy regimen presents a decrease of −50% in term of cell proliferation and −33% in term of cell survival compared to the standard of care. These results are sent to the experimental response's database and will be used by the supervised-learning machine when a similar case will be run.

Six months later, the patient presents a relapse. The tumor molecular profile remaining the same as previously studied, the physician prescribes the association of palbociclib (IBRANCE®, CDK4/6 inhibitor targeting the CDKN2A/B alterations), trametinib (MEKINIST®, MEK1/2 inhibitor targeting the KRAS alteration) and regorafenib (STIVARGA®, multi-kinase inhibitor targeting the TP53 alteration).

Example 6

A 69-year-old over-weight man (Body Mass Index=37.5, clinical obesity class 2) with a 5-year history of type 2 diabetes consults a Diabetes Specialty Clinic in Paris (France) for recent weight gain, foot pain, and persistent nocturia. At the time of his initial appointment, the patient was taking simvastatin (ZOCOR®) for a hyperlipidemia and a "pancreatic elixir" in an attempt to improve his diabetes control. He had been started on glibenclamide (DAONIL®) but had stopped taking it after few months because of dizziness, sweating, and agitation. The laboratory tests performed the same day confirms the uncontrolled type 2 diabetes (evaluated by a level of glycosylated hemoglobin=8.3%-normal<7%), a normo-lipidemia, and an elevated urine micro-albumin level. The physician ordered a urine metabolite profiling. The post-analysis review of the results highlighted the upregulation of the IL-1 (interleukin 1), TNF (Tumor Necrosis Factor), and mTOR (Mammalian Target of Rapamycin) signaling pathways.

Based on the metabolomic profile presented by the patient, the decision-making machine proposes the following bi-therapy regimens (among others):

(1) Canakinumab (ILARIS®, monthly subcutaneous administration), human monoclonal antibody targeting the interleukin-1 beta cytokine (this cytokine has been shown to destruct and cause the loss of function of insulin-producing pancreatic cells); and Metformin (GLUCOPHAGE®, daily oral administration), anti-hyperglycemic bi-guanide, known to specifically inhibit the mTOR pathway by activation of the AMPK (AMP-activated kinase);

or (2) Etanercept (ENBREL®, weekly subcutaneous administration), engineered fusion-protein acting as a decoy receptor for TNF (TNF-alpha plays a role in regulating insulin sensitivity); and Metformin (GLUCOPHAGE®, daily oral administration).

The association of IL-1 and TNF inhibitors together is not considered by the system, as it increases the risk of serious infections. However, the considered regimens do not present any interaction with the simvastatin (ZOCOR®) actually taken and well-tolerated by the patient. All of these drugs are approved by the ANSM (French Agency for Medicines and Medical Products Security).

Additionally to this regimen, the decision-support system recommends optimal dosages (as canakinumab and etanercept may affect the blood level of simvastatin), as well as a reminder for diet and exercise advices (e.g., decrease of carbohydrate intake, 30-minutes fast-pace walk a day, and so on) to provide to the patient.

Example 7

A pharmacology researcher wants to study the effect of a combination of drugs in a human cancer cell-line's proliferation. He previously defined a set of five different targets (A, B, C, D and E) and a library encompassing 150 selective compounds biologically-active against these targets (10 drugs targeting the target A, 25 for B, 30 for C, 40 for D, 40 for E, and 5 drugs targeting simultaneously D and E). He plans to use the decision-support system to define the best combinations to test in a first assay, knowing that he wants to assess all five targets and does not need to filter for targeting redundancies.

Based on this data, the decision-making machine will pick one drug for each of the target, generating a total of 15,187,500 (10×25×30×45×45) combinations. The generation of combination follows the processing steps:

(1) Creation (by picking one drug by target). The total number of combination is defined by:

$\Pi_{i=1}^{N\ targets}(N\ drugs)_{by\ target}$ where N is the number of elements (targets or drugs)

(2) Scoring. In this example, the decision-making machine uses a scoring system based on the activity of each drug against its target, define by the IC50 (half maximal inhibitory concentration). A scale of activity is defined for each {drug-target} pair, with a maximum score of 5 when the activity is at the best level and 0 when the activity is weak. The combination's score is defined by:

$$\frac{\sum_{i=1}^{N\ targets} (\text{score}_{\{drug\text{-}target\}})}{N\ drugs} \text{ where score}_{\{drug\text{-}target\}} \in [0-5]$$

(3) Filtering and data reduction. The first 1000 combinations are randomly created and scored. The decision-making machine defines the median of scores observed for these first set of combination, equal to 3 in this particular case. This number will define the primary threshold to use for the data reduction process. Then, each combination newly created will be scored. If the corresponding score is lower than 3, the combination is discarded. If the corresponding score is greater or equal to 3, the combination is stored with the 1000 others. One combination already stored and presenting the lowest score is discarded and the new threshold/median is calculated (e.g., 3.5). A new combination is created and compared to the median in a similar way that the previous one. This process continues until all 15,187,500 combinations are created, scored and possibly stored. Only 1,000 combinations are stored during the entire process, and only the top 1,000 best combinations (i.e., presenting the highest scores) are kept.

(4) Sorting. The researcher decides to sort the 1,000 remaining combinations by number of drugs used and then by score descending. The final result presented by the web-interface will include all combinations of four drugs ordered from the maximum to the minimal score, followed by all combinations of five drugs in the same order.

Having provided various devices, systems, and methods for personalized medicine, the description now turns to a brief discussion of an example of a computer system on which personalized medicine techniques and systems described herein may be implemented.

Figure 12:
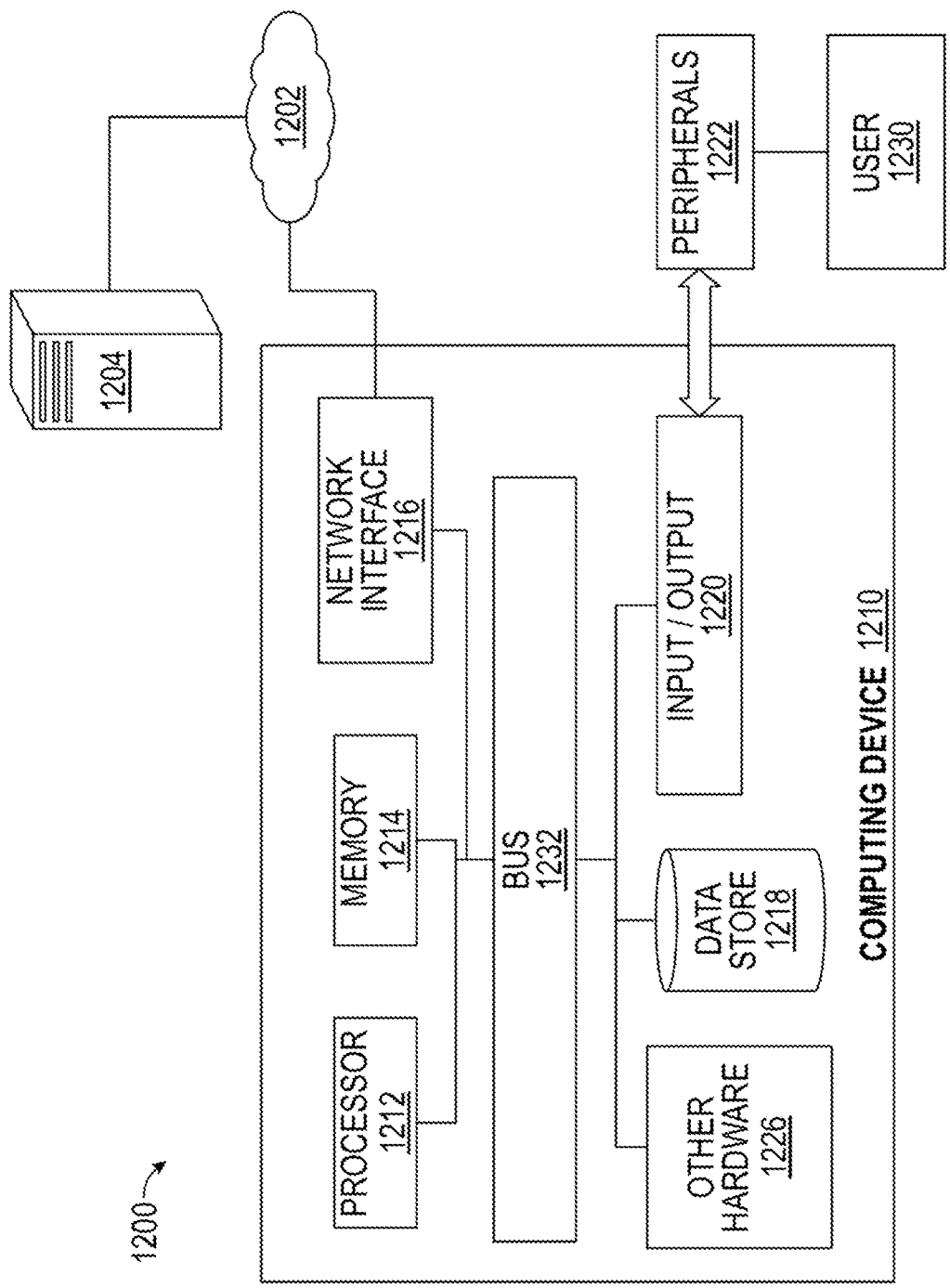
FIG. 12 illustrates a computer system.

FIG. 12 illustrates a computer system. The computer system 1200 may be part of, or otherwise implemented with, the environment for personalized medicine, e.g., described with reference to FIG. 1A above. For example, the computer system 1200 may be the data processing machine, the decision making machine, the learning machines, and the like described with reference to FIG. 1A above, or the computer system 1200 may otherwise be included as part of any of those machines. In an aspect, a computing device 1210 of the computer system 1200 is a network device operated by one or more users (e.g., physician or patient) in the system shown in FIG. 1A. In certain aspects, the computer system 1200 may be implemented using hardware or a combination of software and hardware, either in a dedicated server, or integrated into another entity, or distributed across multiple entities. In general, the computer system 1200 may include a computing device 1210 connected to a network 1202, e.g., through an external device 1204.

The computing device 1210 may include a desktop computer workstation. The computing device 1210 may also or instead be any device suitable for interacting with other devices over a network 1202, such as a laptop computer, a desktop computer, a personal digital assistant, a tablet, a mobile phone, a television, a set top box, a wearable computer, and the like. The computing device 1210 may also or instead include a server or it may be disposed on a server, such as any of the servers described herein.

The computing device 1210 may be used for any of the entities described in the personalized medicine techniques and systems, e.g., as described above with reference to FIG. 1A. In certain aspects, the computing device 1210 may be implemented using hardware (e.g., in a desktop computer), software (e.g., in a virtual machine or the like), or a combination of software and hardware. The computing device 1210 may be a standalone device, a device integrated into another entity or device, a platform distributed across multiple entities, or a virtualized device executing in a virtualization environment.

The network 1202 may include any network described above, e.g., data network(s) or internetwork(s) suitable for communicating data and control information among participants in the computer system 1200. This may include public networks such as the Internet, private networks, and telecommunications networks such as the Public Switched Telephone Network or cellular networks using third generation cellular technology (e.g., 3G or IMT-2000), fourth generation cellular technology (e.g., 4G, LTE. MT-Advanced, E-UTRA, etc.) or WiMax-Advanced (IEEE 802.16m)) and/or other technologies, as well as any of a variety of corporate area, metropolitan area, campus or other local area networks or enterprise networks, along with any switches, routers, hubs, gateways, and the like that might be used to carry data among participants in the computer system 1200. The network 1202 may also include a combination of data networks, and need not be limited to a strictly public or private network.

The external device 1204 may be any computer or other remote resource that connects to the computing device 1210 through the network 1202. This may include personalized medicine resources such as any of those contemplated herein, gateways or other network devices, remote servers or the like containing content requested by the computing device 1210, a network storage device or resource, a device hosting personalized medicine content or data, or any other resource or device that might connect to the computing device 1210 through the network 1202.

In another aspect, the external device 1204 is a server, where the computing device 1210 is a rack within the server. Such a server may include multiple such racks. Also, various servers, which may act in concert to perform processes described herein, may be disposed in different geographic locations. The servers may coordinate their operation in order to provide the capabilities to implement processes described herein. The servers may provide interfaces to other devices including, without limitation, clients, other servers, printers, database servers, print servers, file servers, communication servers, distributed servers, and the like, where any and all of which may be included as another external device 1204 in the computer system 1200. The processes and techniques described herein may be implemented on one such server or on multiple such servers.

In general, the computing device 1210 may include a processor 1212, a memory 1214, a network interface 1216, a data store 1218, and one or more input/output interfaces 1220. The computing device 1210 may further include or be in communication with peripherals 1222 and other external input/output devices that might connect to the input/output interfaces 1220.

The processor 1212 may be any processor or other processing circuitry capable of processing instructions for execution within the computing device 1210 or computer system 1200. The processor 1212 may include a single-threaded processor, a multi-threaded processor, a multi-core processor and so forth. The processor 1212 may be capable of processing instructions stored in the memory 1214 or the data store 1218.

The memory 1214 may store information within the computing device 1210. The memory 1214 may include any volatile or non-volatile memory or other computer-readable medium, including without limitation a Random Access Memory (RAM), a flash memory, a Read Only Memory (ROM), a Programmable Read-only Memory (PROM), an Erasable PROM (EPROM), registers, and so forth. The memory 1214 may store program instructions, program data, executables, and other software and data useful for controlling operation of the computing device 1210 and configuring the computing device 1210 to perform functions for a user. The memory 1214 may include a number of different stages and types of memory for different aspects of operation of the computing device 1210. For example, a processor may include on-board memory and/or cache for faster access to certain data or instructions, and a separate, main memory or the like may be included to expand memory capacity as desired. All such memory types may be a part of the memory 1214 as contemplated herein.

The memory 1214 may, in general, include a non-volatile computer readable medium containing computer code that, when executed by the computing device 1210 creates an execution environment for a computer program in question, e.g., code that constitutes processor firmware, a protocol stack, a database management system, an operating system, or a combination of the foregoing, and/or code that performs some or all of the steps set forth in the various flow charts and other algorithmic descriptions set forth herein. While a single memory 1214 is depicted, it will be understood that any number of memories may be usefully incorporated into the computing device 1210. For example, a first memory may provide non-volatile storage such as a disk drive for permanent or long-term storage of files and code even when the computing device 1210 is powered down. A second memory such as a random access memory may provide volatile (but higher speed) memory for storing instructions and data for executing processes. A third memory may be used to improve performance by providing higher speed memory physically adjacent to the processor 1212 for registers, caching, and so forth. The processor 212 and the memory 214 can be supplemented by, or incorporated in, logic circuitry.

The network interface 1216 may include any hardware and/or software for connecting the computing device 1210 in a communicating relationship with other resources through the network 1202. This may include remote resources accessible through the Internet, as well as local resources available using short range communications protocols using, e.g., physical connections (e.g., Ethernet), radio frequency communications (e.g., WiFi), optical communications, (e.g., fiber optics, infrared, or the like), ultrasonic communications, or any combination of these or other media that might be used to carry data between the computing device 1210 and other devices. The network interface 1216 may, for example, include a router, a modem, a network card, an infrared transceiver, a radio frequency (RF) transceiver, a near field communications interface, a radio-frequency identification (RFID) tag reader, or any other data reading or writing resource or the like.

More generally, the network interface 1216 may include any combination of hardware and software suitable for coupling the components of the computing device 1210 to other computing or communications resources. By way of example and not limitation, this may include electronics for a wired or wireless Ethernet connection operating according to the IEEE 802.11 standard (or any variation thereof), or any other short or long range wireless networking components or the like. This may include hardware for short range data communications such as Bluetooth or an infrared transceiver, which may be used to couple to other local devices, or to connect to a local area network or the like that is in turn coupled to a data network 1202 such as the Internet. This may also or instead include hardware/software for a WiMax connection or a cellular network connection (using, e.g., CDMA, GSM, LTE, or any other suitable protocol or combination of protocols). The network interface 1216 may be included as part of the input/output devices 1220 or vice-versa.

The data store 1218 may be any internal memory store providing a computer-readable medium such as a disk drive, an optical drive, a magnetic drive, a flash drive, or other device capable of providing mass storage for the computing device 1210. The data store 1218 may store computer readable instructions, data structures, program modules, and other data for the computing device 1210 or computer system 1200 in a non-volatile form for subsequent retrieval and use. For example, the data store 1218 may store without limitation one or more of the operating system, application programs, program data, databases, files, and other program modules or other software objects and the like.

The input/output interface 1220 may support input from and output to other devices that might couple to the computing device 1210. This may, for example, include serial ports (e.g., RS-232 ports), universal serial bus (USB) ports, optical ports, Ethernet ports, telephone ports, audio jacks, component audio/video inputs, HDMI ports, and so forth, any of which might be used to form wired connections to other local devices. This may also or instead include an infrared interface, RF interface, magnetic card reader, or other input/output system for coupling in a communicating relationship with other local devices. It will be understood that, while the network interface 1216 for network communications is described separately from the input/output interface 1220 for local device communications, these two interfaces may be the same, or may share functionality, such as where a USB port is used to attach to a WiFi accessory, or where an Ethernet connection is used to couple to a local network attached storage.

A peripheral 1222 may include any device used to provide information to or receive information from the computing device 1200. This may include human input/output (I/O) devices such as a keyboard, a mouse, a mouse pad, a track ball, a joystick, a microphone, a foot pedal, a camera, a touch screen, a scanner, or other device that might be employed by the user 1230 to provide input to the computing device 1210. This may also or instead include a display, a speaker, a printer, a projector, a headset or any other audiovisual device for presenting information to a user. The peripheral 1222 may also or instead include a digital signal processing device, an actuator, or other device to support control or communication to other devices or components. Other I/O devices suitable for use as a peripheral 1222 include haptic devices, three-dimensional rendering systems, augmented-reality displays, magnetic card readers, and so forth. In one aspect, the peripheral 1222 may serve as the network interface 1216, such as with a USB device configured to provide communications via short range (e.g., BlueTooth, WiFi, Infrared, RF, or the like) or long range (e.g., cellular data or WiMax) communications protocols. In another aspect, the peripheral 1222 may provide a device to augment operation of the computing device 1210, such as a global positioning system (GPS) device, a security dongle, or the like. In another aspect, the peripheral may be a storage device such as a flash card, USB drive, or other solid state device, or an optical drive, a magnetic drive, a disk drive, or other device or combination of devices suitable for bulk storage. More generally, any device or combination of devices suitable for use with the computing device 1200 may be used as a peripheral 1222 as contemplated herein.

Other hardware 1226 may be incorporated into the computing device 1200 such as a co-processor, a digital signal processing system, a math co-processor, a graphics engine, a video driver, and so forth. The other hardware 1226 may also or instead include expanded input/output ports, extra memory, additional drives (e.g., a DVD drive or other accessory), and so forth.

A bus 1232 or combination of busses may serve as an electromechanical platform for interconnecting components of the computing device 1200 such as the processor 1212, memory 1214, network interface 1216, other hardware 1226, data store 1218, and input/output interface. As shown in the figure, each of the components of the computing device 1210 may be interconnected using a system bus 1232 or other communication mechanism for communicating information.

Methods and systems described herein may be realized using the processor 1212 of the computer system 1200 to execute one or more sequences of instructions contained in the memory 1214 to perform predetermined tasks. In embodiments, the computing device 1200 may be deployed as a number of parallel processors synchronized to execute code together for improved performance, or the computing device 1200 may be realized in a virtualized environment where software on a hypervisor or other virtualization management facility emulates components of the computing device 1200 as appropriate to reproduce some or all of the functions of a hardware instantiation of the computing device 1200.

The coupling and/or connection between components in the computer system 1200, such as those described above, may facilitate remote execution of programs across the network 1202. In this manner, the networking of some or all of these devices may facilitate parallel processing of a program or a method at one or more location without deviating from the scope of the implementations described herein. In addition, any of the devices attached to components in the computer system 1200 (e.g., a server) through an interface may include at least one storage medium capable of storing methods, programs, code and/or instructions. A central repository may provide program instructions to be executed on different devices. In such an implementation, the remote repository may act as a storage medium for program code, instructions, and programs.

Implementations described herein can be implemented using a computer system 200 in response to the processor 1212 executing one or more sequences of one or more instructions contained in the memory 1214. Such instructions may be read into the memory 1214 from another machine-readable medium, such as the data store 1218. Execution of the sequences of instructions contained in the memory 1214 may cause the processor 1212 to perform processes described herein. One or more processors 1212 in a multi-processing arrangement may also be employed to execute the sequences of instructions contained in the memory 1214. In alternative aspects, hard-wired circuitry may be used in place of or in combination with software instructions to implement various aspects of the present disclosure. Thus, aspects of the present disclosure are not limited to any specific combination of hardware circuitry and software.

Example 8—Cloud Implementation

The proposed system can be implemented to run in one of the computational environments offered by a cloud provider. Such implementation can fully utilize low to medium level interfaces accessible by the underlying layers to interact with users, process input requests, store and retrieve necessary data. It accommodates all input-output processing and calculation requiring only business logic implementation and not the standard system routines, such as serving various standard protocols.

In the proposed solution, Java computer language was chosen to better utilize the existing enterprise frameworks to focus on high availability and the ease of code implementation, support and deployment in the modern heterogeneous computational infrastructures. All modules and interfaces, including user-interface of the system are bundled together by the Jenkins build system as Enterprise Application and archived for ease of deployment.

Figure 13:
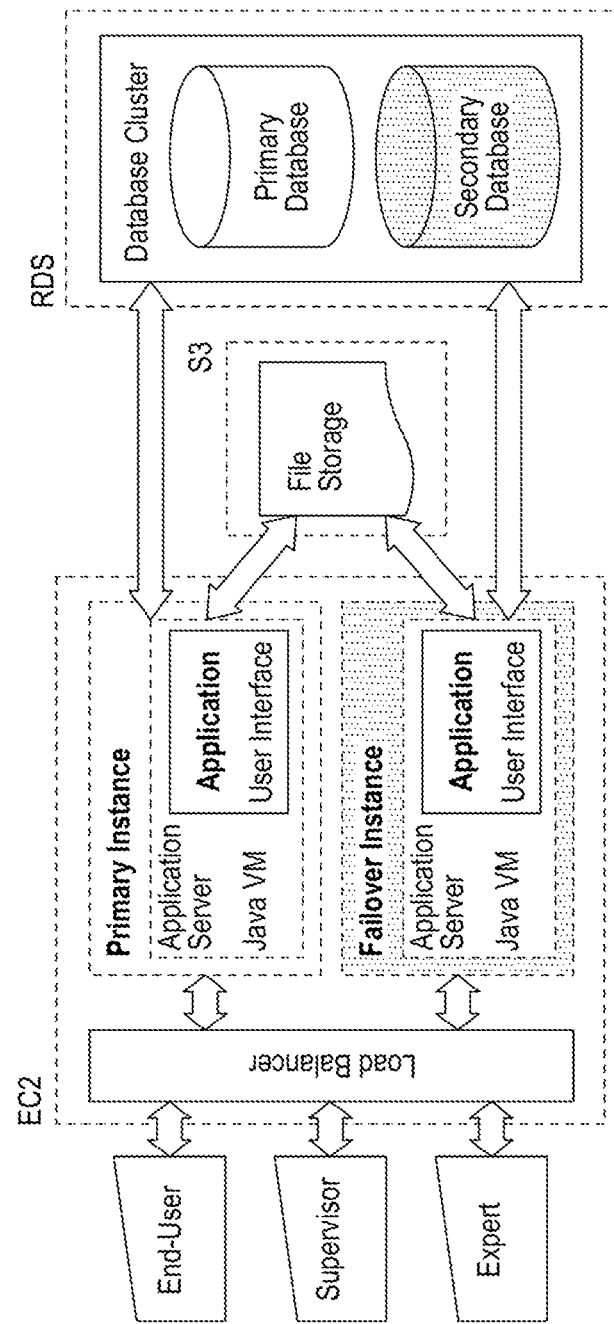
FIG. 13 illustrates a cloud computing system.

For example in the FIG. 13, the block diagram illustrates the implemented application deployed into the configured enterprise container on one of the Elastic Compute Cloud (EC2) Virtual Machine (VM) instances configured in the cloud solution (e.g. Amazon Web Services, Google Cloud . . . ). In order to address fault-tolerance demands, more than one computational instances proposed for production deployment may be used. Such virtual instances must be identically configured to run the Linux operating system with the same number of available central processing unit (CPU) cores, memory and hard drive capacity. Each instance has a configured enterprise Java server container running to serve the application for the proposed system with high availability. In this example the most up-to-date Apache Tomcat 8.0 container and Java JDK 8 are used.

Only one application server on the primary instance is serving requests to the application via the load balancer to guarantee that service is provided at all times. In case of failure in one or more instances, requests will be routed to the back-up fail-over instance. The cloud provider guarantees high availability by scaling the number of configured primary instances to address high volumes of usage and recovery procedures for failed instances.

The implemented application communicates with a database configured in the cluster for storing and retrieving necessary data. Any Structured Query Language (SQL) compatible with SQL92 relational database services supporting the Java Database Connectivity (JDBC) protocol for communication such as Microsoft SQL Server, Oracle, PostgreSQL or MySQL can be used. In this example we rely on Aurora SQL database provided by Amazon Web Services in the Amazon Relational Database Service (RDS) environment. This Aurora database server is similar to the MySQL database server, but oriented towards ease of setup and deployment in a fault-tolerant cloud-based cluster environment. In the provided example, the database cluster utilizes at least two instances running the Linux Operating System and running database services with data replication from primary to fail-over nodes to provide uninterrupted database access. For high availability multiple primary nodes can be added to address high volumes of requests. The data storage is encrypted to provide increased security.

In the provided example, the application utilizes file storage buckets in the Amazon Simple Storage Service (S3) environment for secure access to large amounts of data required for processing by various subsystems of Application of proposed system.

All the communication within the cloud infrastructure between EC2, S3 and RDS is performed securely to protect all vital information within an isolated "secure group". End-users and system supervisors, including experts access the system via web-based interface and provide all the necessary input information. In the proposed example Hyper Text Transport Protocol Secure (HTTPS) protocol is used to protect all inbound and outbound communication with the Load Balancer configuration.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

The systems and methods disclosed herein may be implemented via one or more components, systems, servers, appliances, other subcomponents, or distributed between such elements. When implemented as a system, such systems may include an/or involve, inter alia, components such as software modules, general-purpose CPU, RAM, etc., found in general-purpose computers. In implementations where the innovations reside on a server, such a server may include or involve components such as CPU, RAM, etc., such as those found in general-purpose computers.

Additionally, the systems and methods herein may be achieved via implementations with disparate or entirely different software, hardware and/or firmware components, beyond that set forth above. With regard to such other components (e.g., software, processing components, etc.) and/or computer-readable media associated with or embodying the present implementations, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the systems and methods may be achieved via or performed by logic and/or logic instructions including program modules, executed in association with such components or circuitry, for example. In general, program modules may include routines, programs, objects, components, data structures, etc., that perform particular tasks or implement particular instructions herein. The embodiments may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, where media of any type herein does not include transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the implementations described herein or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the implementations herein, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

Moreover, the above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method for identifying new therapeutic options based on matching combinations of available drugs to a patient's molecular profile comprising one or more molecular biomarkers, the method comprising:
   a) obtaining patient data for a patient, the patient data including one or more molecular biomarkers specific to the patient;
   b) processing the patient data to obtain standardized patient data;
   c) classifying the standardized patient data including classifying the one or more molecular biomarkers by one or more of its functional effects, thereby generating a list of curated biomarkers functionally impacting a disease of the patient or relevant to a therapeutic decision for the patient;
   d) generating, scoring and sorting therapeutic options comprising new combination therapies using functional effects for molecular biomarkers from the list of curated biomarkers, wherein generating, scoring and sorting therapeutic options comprise the following steps:
      (i) listing available drugs that are related to functional effects of each biomarker from the list of curated biomarkers;
      (ii) generating a number of therapeutic options acting on biomarkers from the list of curated biomarkers by combining the available drugs listed for each biomarker from the list of curated biomarkers;
      (iii) filtering out potentially unwanted therapeutic options from the generated therapeutic options by querying a database containing known or predictable negative interactions, or containing drug toxicity data;
      (iv) scoring therapeutic options remaining after the filtering step based on at least an efficiency-toxicity balance for each therapeutic option, thereby producing a numerical or qualitative score for each therapeutic option remaining after the filtering step;
      (v) optionally, setting a threshold score for generated therapeutic options and filtering out therapeutic options having scores that do not meet or exceed the threshold score;
      (vi) sorting therapeutic options remaining after steps (iii)-(v) by one or more relevant criteria selected by a user, wherein the one or more relevant criteria comprise at least one of the following: the numerical or qualitative score of a given therapeutic option generated on the step (iv), a number of drugs in a given therapeutic option, a number of biomarkers covered by a given therapeutic option, the number of biomarkers from the list of curated biomarkers not covered by a given therapeutic option, a presence of acceptable targeting redundancies, a presence of pharmacological class redundancies;
   thereby identifying an optimized list of therapeutic options that target biomarkers from the list of curated biomarkers;
   e) optionally, reducing the optimized list of therapeutic options identified in step d) for presentation to a user based on a criterion, wherein the criterion includes one or more of a level of confidence, a maximum number of drugs, and a minimum number of drugs;
   f) presenting the optimized list of therapeutic options to the user.

2. The method of claim 1, wherein the patient data includes a medical history and demographics data, wherein the medical history and demographics data includes one or more of age, gender, a histological diagnosis, a previous treatment, a current treatment, a comorbidity, a familial history, and an inherited syndrome.

3. The method of claim 1, wherein the one or more molecular biomarkers is obtained via at least one of: a biopsy;
   an external resource;
   transcriptomic profiling, wherein the transcriptomic profiling includes one or more of a microarray, RNA sequencing, real-time polymerase amplification;
   genomic profiling, wherein the genomic profiling includes one or more of histone modification assay, chromatin immunoprecipitation, restriction landmark analysis, bisulfate sequencing;
   proteomic profiling, wherein proteomic profiling includes one or more of an immunoassay and mass spectrometry; and
   one or more of metabolomics profiling and biochemistry profiling.

4. The method of claim 1, wherein step e) further comprises: applying a learning method to further optimize the generated therapeutic options for presentation to the user, the learning method including at least one of: a first learning method comprising:
   querying a clinical outcome database for similar cases, the clinical outcome database including records comprising a diagnosis, a set of biomarkers, one or more recommended therapeutic options, and an outcome obtained after treatment by the one or more recommended therapeutic options;
   comparing the generated therapeutic options to the similar cases; and
   eliminating therapeutic options that do not satisfy a threshold of similarity; and
   a second learning method comprising comparing efficacies of the generated therapeutic options to an efficacy of one or more similar therapeutic options based on an experimental model.

5. The method of claim 1, wherein classifying the one or more molecular biomarkers includes querying a database of gene functional effect information.

6. The method of claim 1, wherein
   at step d) (ii), the number of therapeutic options is generated by multiplying numbers of the available drugs listed for each biomarker from the list of curated biomarkers that has at least one available drug listed in step d) (i) by each other.

7. The method of claim 1, wherein therapeutic options produced at step d) (ii) act on each biomarker from the list of curated biomarkers.

8. The method of claim 1, wherein presenting the optimized list of therapeutic options to the user comprises:
displaying the optimized list of therapeutic options in a user interface hosted by a web server; and
presenting the optimized list of therapeutic options in a report.

9. The method of claim 1, further comprising:
recommending a specific dosage of each drug in the optimized list of therapeutic options.

10. A computer program product comprising computer executable code embodied in a non-transitory computer readable medium that, when executing on one or more computing devices, performs the steps of:
a) obtaining patient data for a patient, the patient data including one or more molecular biomarkers specific to the patient;
b) processing the patient data to obtain standardized patient data;
c) classifying the standardized patient data including classifying the one or more molecular biomarkers by one or more of its functional effects, thereby generating a list of curated biomarkers functionally impacting a disease of the patient or relevant to a therapeutic decision for the patient;
d) generating, scoring and sorting therapeutic options comprising new combination therapies using functional effects for molecular biomarkers from the list of curated biomarkers, wherein generating, scoring and sorting therapeutic options comprise the following steps:
(i) listing available drugs that are related to functional effects of each biomarker from the list of curated biomarkers;
(ii) generating a number of therapeutic options acting on biomarkers from the list of curated biomarkers by combining the available drugs listed for each biomarker from the list of curated biomarkers;
(iii) filtering out potentially unwanted therapeutic options from the generated therapeutic options by querying a database containing known or predictable negative interactions, or containing drug toxicity data;
(iv) scoring therapeutic options remaining after the filtering step based on at least an efficiency-toxicity balance for each therapeutic option, thereby producing a numerical or qualitative score for each therapeutic option remaining after the filtering step;
(v) optionally, setting a threshold score for generated therapeutic options and filtering out therapeutic options having scores that do not meet or exceed the threshold score;
(vi) sorting therapeutic options remaining after steps (iii)-(v) by one or more relevant criteria selected by a user, wherein the one or more relevant criteria comprise at least one of the following: the numerical or qualitative score of a given therapeutic option generated on the step (iv), a number of drugs in a given therapeutic option, a number of biomarkers covered by a given therapeutic option, the number of biomarkers from the list of curated biomarkers not covered by a given therapeutic option, a presence of acceptable targeting redundancies, a presence of pharmacological class redundancies;
thereby identifying an optimized list of therapeutic options that target biomarkers from the list of curated biomarkers;
e) optionally, reducing the optimized list of therapeutic options identified in step d) for presentation to a user based on a criterion, wherein the criterion includes one or more of a level of confidence, a maximum number of drugs, and a minimum number of drugs;
f) presenting the optimized list of therapeutic options to the user.

11. A system comprising:
a server;
a computing device in communication with the server over a network, the computing device including a processor and a memory, the memory bearing computer executable code configured to perform the steps of:
a) obtaining patient data for a patient, the patient data including one or more molecular biomarkers specific to the patient;
b) processing the patient data to obtain standardized patient data;
c) classifying the standardized and curated patient data including classifying the one or more molecular biomarkers by one or more of its functional effects, thereby generating a list of curated biomarkers functionally impacting a disease of the patient or relevant to a therapeutic decision for the patient;
d) generating, scoring and sorting therapeutic options comprising new combination therapies using functional effects for molecular biomarkers from the list of curated biomarkers, wherein generating, scoring and sorting therapeutic options comprise the following steps:
(i) listing available drugs that are related to functional effects of each biomarker from the list of curated biomarkers;
(ii) generating a number of therapeutic options acting on biomarkers from the list of curated biomarkers by combining the available drugs listed for each biomarker from the list of curated biomarkers;
(iii) filtering out potentially unwanted therapeutic options from the generated therapeutic options by querying a database containing known or predictable negative interactions, or containing drug toxicity data;
(iv) scoring therapeutic options remaining after the filtering step based on at least an efficiency-toxicity balance for each therapeutic option, thereby producing a numerical or qualitative score for each therapeutic option remaining after the filtering step;
(v) optionally, setting a threshold score for generated therapeutic options and filtering out therapeutic options having scores that do not meet or exceed the threshold score;
(vi) sorting therapeutic options remaining after steps (iii)-(v) by one or more relevant criteria selected by a user, wherein the one or more relevant criteria comprise at least one of the following: the numerical or qualitative score of a given therapeutic option generated on the step (iv), a number of drugs in a given therapeutic option, a number of biomarkers covered by a given therapeutic option, the number of biomarkers from the list of curated biomarkers not covered by a given therapeutic option, a presence of acceptable targeting redundancies, a presence of pharmacological class redundancies;
thereby identifying an optimized list of therapeutic options that target biomarkers from the list of curated biomarkers;
e) optionally, reducing the optimized list of therapeutic options identified in step d) for presentation to a user based on a criterion, wherein the criterion includes one or more of a level of confidence, a maximum number of drugs, and a minimum number of drugs;

f) presenting the optimized list of therapeutic options to the user.

\* \* \* \* \*